United States Patent
Miller et al.

(10) Patent No.: US 11,920,169 B2
(45) Date of Patent: Mar. 5, 2024

(54) COMPOSITIONS FOR LINKING DNA-BINDING DOMAINS AND CLEAVAGE DOMAINS

(71) Applicant: Sangamo Therapeutics, Inc., Brisbane, CA (US)

(72) Inventors: Jeffrey C. Miller, Brisbane, CA (US); David Paschon, Brisbane, CA (US); Edward J. Rebar, Brisbane, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 531 days.

(21) Appl. No.: 16/906,845

(22) Filed: Jun. 19, 2020

(65) Prior Publication Data
US 2020/0318087 A1   Oct. 8, 2020

Related U.S. Application Data

(62) Division of application No. 15/380,784, filed on Dec. 15, 2016, now Pat. No. 10,724,020.

(60) Provisional application No. 62/290,065, filed on Feb. 2, 2016.

(51) Int. Cl.
| | | |
|---|---|---|
| *C12N 9/22* | (2006.01) | |
| *C12N 15/52* | (2006.01) | |
| *C12N 15/62* | (2006.01) | |
| *C12N 15/90* | (2006.01) | |

(52) U.S. Cl.
CPC .............. *C12N 9/22* (2013.01); *C12N 15/52* (2013.01); *C12N 15/62* (2013.01); *C12N 15/907* (2013.01); *C12Y 301/00* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,897,355 A | 1/1990 | Eppstein et al. |
| 4,946,787 A | 8/1990 | Eppstein et al. |
| 5,049,386 A | 9/1991 | Eppstein et al. |
| 5,356,802 A | 10/1994 | Chandrasegaran |
| 5,420,032 A | 5/1995 | Marshall et al. |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox et al. |
| 6,599,692 B1 | 7/2003 | Case et al. |
| 6,607,882 B1 | 8/2003 | Cox et al. |
| 6,689,558 B2 | 2/2004 | Case et al. |
| 6,723,551 B2 | 4/2004 | Kotin et al. |
| 6,824,978 B1 | 11/2004 | Cox et al. |
| 6,833,252 B1 | 12/2004 | Dujon et al. |
| 6,903,185 B2 | 6/2005 | Kim et al. |
| 6,933,113 B2 | 8/2005 | Case et al. |
| 6,979,539 B2 | 12/2005 | Cox et al. |
| 7,013,219 B2 | 3/2006 | Case et al. |
| 7,067,317 B2 | 6/2006 | Rebar et al. |
| 7,153,949 B2 | 12/2006 | Kim et al. |
| 7,163,824 B2 | 1/2007 | Cox et al. |
| 7,262,054 B2 | 8/2007 | Jamieson et al. |
| 7,271,002 B2 | 9/2007 | Kotin et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller |
| 8,110,379 B2 | 2/2012 | DeKelver et al. |
| 8,409,861 B2 | 4/2013 | Guschin et al. |
| 8,586,526 B2 | 11/2013 | Gregory et al. |
| 8,623,618 B2 | 1/2014 | Doyon et al. |
| 8,697,359 B1 | 4/2014 | Zhang |
| 8,703,489 B2 | 4/2014 | Wang |
| 8,772,453 B2 | 7/2014 | Paschon et al. |

(Continued)

FOREIGN PATENT DOCUMENTS

| | | |
|---|---|---|
| GB | 2338237 A | 12/1999 |
| JP | 2011-521643 A | 7/2011 |

(Continued)

OTHER PUBLICATIONS

Argast, et al., "I-Ppol AND I-Crel Homing Site Sequence Degeneracy Determined By Random Mutagenesis and Sequential in Vitro ENRICHMENT," *Journal of Molecular Biology* 280:345-353 (1998).
Ashworth, et al., "Computational Redesign of Endonuclease DNA Binding and Cleavage Specificity," *Nature* 441:656-659 (2006).
Beerli, et al., "Engineering Polydactyl Zinc-Finger Transcription Factors," *Nature Biotechnology* 20:135-141 (2002).
Belfort, et al., "Homing Endonucleases: Keeping the House in Order," *Nucleic Acids Research* 25(17):3379-3388 (1997).

(Continued)

*Primary Examiner* — Brent T Page
(74) *Attorney, Agent, or Firm* — Foley & Lardner LLP

(57) ABSTRACT

Disclosed herein are compositions for linking DNA binding domains and cleavage domains (or cleavage half-domains) to form non-naturally occurring nucleases with alternative configurations. Also described are methods of making and using compositions comprising these linkers.

34 Claims, 20 Drawing Sheets

Specification includes a Sequence Listing.

(56) References Cited

U.S. PATENT DOCUMENTS

| | | |
|---|---|---|
| 8,945,868 B2 | 2/2015 | Collingwood et al. |
| 8,956,828 B2 | 2/2015 | Bonini et al. |
| 9,005,973 B2 | 4/2015 | Cost et al. |
| 9,045,763 B2 | 6/2015 | DeKelver et al. |
| 9,255,250 B2 | 2/2016 | Gregory et al. |
| 9,394,531 B2 | 7/2016 | Miller |
| 9,458,205 B2 | 10/2016 | Gregory et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2006/0063231 A1 | 3/2006 | Li et al. |
| 2006/0188987 A1 | 8/2006 | Guschin et al. |
| 2007/0117128 A1 | 5/2007 | Smith et al. |
| 2007/0150973 A1 | 6/2007 | Pomerantz et al. |
| 2007/0218528 A1* | 9/2007 | Miller ............... C07K 14/4702 435/325 |
| 2008/0159996 A1 | 7/2008 | Ando et al. |
| 2009/0068164 A1 | 3/2009 | Segal et al. |
| 2009/0305419 A1 | 12/2009 | Miller |
| 2010/0218264 A1 | 8/2010 | Cui et al. |
| 2011/0201055 A1 | 8/2011 | Doyon et al. |
| 2011/0265198 A1 | 10/2011 | Gregory et al. |
| 2011/0301073 A1 | 12/2011 | Gregory et al. |
| 2012/0017290 A1 | 1/2012 | Cui et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2014/0335063 A1 | 11/2014 | Cannon et al. |
| 2015/0044772 A1 | 2/2015 | Zhao |
| 2015/0056705 A1 | 2/2015 | Conway et al. |
| 2015/0064789 A1 | 3/2015 | Paschon et al. |
| 2015/0071898 A1 | 3/2015 | Liu et al. |

FOREIGN PATENT DOCUMENTS

| | | |
|---|---|---|
| WO | WO 1991/16024 A1 | 10/1991 |
| WO | WO 1991/17424 A1 | 11/1991 |
| WO | WO 1995/19431 A1 | 7/1995 |
| WO | WO 1996/06166 A1 | 2/1996 |
| WO | WO 1998/37186 A1 | 8/1998 |
| WO | WO 1998/53057 A1 | 11/1998 |
| WO | WO 1998/53058 A1 | 11/1998 |
| WO | WO 1998/53059 A1 | 11/1998 |
| WO | WO 1998/53060 A1 | 11/1998 |
| WO | WO 1998/54311 A1 | 12/1998 |
| WO | WO 2000/27878 A1 | 5/2000 |
| WO | WO 2001/60970 A2 | 8/2001 |
| WO | WO 2001/88197 A2 | 11/2001 |
| WO | WO 2002/016536 A1 | 2/2002 |
| WO | WO 2002/099084 A2 | 12/2002 |
| WO | WO 2003/016496 A2 | 2/2003 |
| WO | WO 2007/139982 A2 | 6/2007 |
| WO | WO 2009/054985 A1 | 4/2009 |
| WO | WO-2009/154686 A1 | 12/2009 |
| WO | WO 2010/079430 A1 | 7/2010 |
| WO | WO-2012/138901 A1 | 10/2012 |
| WO | WO 2012/138901 A1 | 10/2012 |
| WO | WO 2013/045480 A1 | 4/2013 |
| WO | 2015027134 A1 | 2/2015 |
| WO | 2015035136 A2 | 3/2015 |
| WO | WO 2015/031619 A1 | 3/2015 |

OTHER PUBLICATIONS

Beurdeley, et al., "Compact Designer Talens for Efficient Genome Engineering," *Nat Comm*: 1-8 doi: 10.1038/ncomms2782 (2013).
Bibikova, et al., "Stimulation of Homologous Recombination Through Targeted Cleavage By Chimeric Nucleases," *Molecular and Cell Biology* 21(1):289-297 (2001).
Boch, et al., "Breaking the Code of DNA Binding Specificity of Tal-Type III Effectors," *Science* 326:1509-1512 (2009).
Bonas, et al., "Genetic and Structural Characterization of the Avirulence Gene avrBs3 From *Xanthomonas campestris* pv. *vesicatoria,*" *Molecular and General Genetics* 218:127-136 (1989).
Chevalier, et al., "Design, Activity, and Structure of a Highly Specific Artificial Endonuclease," *Molecular Cell* 10:895-905 (2002).
Choo, et al., "Advances in Zinc Finger Engineering," *Curr. Opin. Struct. Biol.* 10:411-416 (2000).
Christian, et al., "Targeting DNA Double-Strand Breaks With Tal Effector Nucleases," *Genetics* 186:757-761 (2010) ePub 10.1534/genetics.110.120717.
Cong, et al., "Multiplex Genome Engineering Using CRISPR/Cas SYSTEMS," *Science* 339(6121):819-823 (2013) doi: 10.1126/science.1231143.
Dujon, et al., "Mobile Introns: Definition of Terms and Recommended Nomenclature," *Gene* 82:115-118 (1989).
Epinat, et al., "A Novel Engineered Meganuclease Induces Homologous Recombination in Yeast and Mammalian Cells," *Nucleic Acids Research* 31(11):2952-2962 (2003).
Gimble, et al., "Substrate Recognition and Induced DNA Distortion By The PI-Scel Endonuclease, an Enzyme Generated By Protein Splicing," *Journal of Molecular Biology* 263: 163-180 (1996).
Guo, et al., "Directed Evolution of an Enhanced and Highly Efficient FokI Cleavage Domain for Zinc Finger Nucleases," *Journal of Molecular Biology* 400(1):96-107 (2010).
Hackett, et al., "*Sleeping Beauty* Transposon-Mediated Gene Therapy for Prolonged Expression," *Advances in Genetics* 54:189-232 (2005).
Haft, et al., "A Guild Of 45 CRISPR-ASSOCIATED (Cas) Protein Families and Multiple CRISPR/Cas Subtypes Exist in Prokaryotic Genomes," *PLoS Computational Biology* 1(6):e60 (2005).
Händel, et al., "Expanding or Restricting the Target Site Repertoire of Zinc-Finger Nucleases: the Inter-Domain Linker as a Major Determinant of Target Site Selectivity," *Mol Ther* 17(1):104-11 (2009).
Heuer, et al., "Repeat Domain Diversity Of avrBs3-like Genes In *Ralstonia solanacearum* Strains and Association With Host Preferences in the Field," *Applied and Environmental Microbiology* 73(13):4379-4384 (2007).
Isalan, et al., "A Rapid, Generally Applicable Method To Engineer Zinc Fingers Illustrated By Targeting the HIV-1 Promoter," *Nature Biotechnology* 19:656-660 (2001).
Jansen, et al., "Identification of Genes That Are Associated With DNA Repeats in Prokaryotes," *Molecular Microbiology* 43(6):1565-1575 (2002).
Jasin, et al., "Genetic Manipulation of Genomes With Rare-Cutting Endonucleases," *Trends in Genetics* 12(6):224-228 (1996).
Kay, et al., "A Bacterial Effector Acts as a Plant Transcription Factor and Induces a Cell Size Regulator," *Science* 318:648-651 (2007).
Kim, et al., "Chimeric Restriction Endonuclease," *Proc. Natl. Acad. Sci. U.S.A.* 90:883-887 (1994).
Kim, et al., "Insertion and Deletion Mutants Of FokI Restriction Endonuclease," *Journal of Biological Chemistry* 269(50):31978-31982 (1994).
Li, et al., "Alteration of the Cleavage Distance Of Fok I Restriction Endonuclease By Insertion Mutagenesis," *Proc. Natl. Acad. Sci. U.S.A.* 90:2764-2768 (1993).
Li, et al., "Functional Domains In Fok I Restriction Endonuclease," *Proc. Natl. Acad. Sci. U.S.A.* 89:4275-4279 (1992).
Makarova, et al., "A DNA Repair System Specific for Thermophilic Archaea and Bacteria Predicted By Genomic Context Analysis," *Nucleic Acids Research* 30:482-496 (2002).
Makarova, et al., "A Putative RNA-Interference-Based Immune System in Prokaryotes: Computational Analysis of the Predicted Enzymatic Machinery, Functional Analogies With Eukaryotic RNAi, And Hypothetical Mechanisms of Action," *Biol. Direct* 1:7 (2006).
Moscou, et al., "A Small Cipher Governs DNA Recognition By Tal Effectors," *Science* 326:1501 (2009).
Olovnikov, et al., "Bacterial Argonaute Samples the Transcriptome To Identify Foreign DNA," *Molecular Cell* 51:594-605 (2013).
Pabo, et al., "Design and Selection of Novel CYS2-HIS2 Zinc Finger Proteins," *Ann. Rev. Biochem.* 70:313-340 (2001).
Paques, et al., "Meganucleases and DNA Double-Strand Break-Induced Recombination: Perspectives for Gene Therapy," *Current Gene Therapy* 7:49-66 (2007).

(56) References Cited

OTHER PUBLICATIONS

Perler, et al., "Protein Splicing Elements: Inteins and Exteins—A Definition of Terms and Recommended Nomenclature," *Nucleic Acids Research* 22(7):1125-1127 (1994).
Schornack, et al., "Gene-For-Gene-Mediated Recognition of Nuclear-Targeted AvrBs3-like Bacterial Effector Proteins," *Journal of Plant Physiology* 163(3):256-272 (2006).
Segal, et al., "Custom DNA-Binding Proteins Come of Age: Polydactyl Zinc-Finger Proteins," *Curr. Opin. Biotechnol.* 12:632-637 (2001).
Sheng, et al., "Structure-Based Cleavage Mechanism Of *Thermus thermophilus* Argonaute DNA Guide Strand-Mediated DNA Target Cleavage," *Proc. Natl. Acad. Sci. U.S.A.* 111(2):652-657 (2014).
Smith, et al., "Requirements for Double-Strand Cleavage By Chimeric Restriction Enzumes With Zinc Finger DNA-Recognition Domains," *Nucleic Acids Research* 28(17):3361-3369 (2000).
Swarts, et al., "DNA-Guided DNA Interference By a Prokaryotic Argonaute" *Nature* 507(7491):258-261 (2014).
Vogel, "A Bacterial Seek-And-Destroy System for Foreign DNA," *Science* 344(6187):972-973 (2014).
Yuan, et al., "Crystal Structure of *A. aeolicus* Argonaute, a Site-Specific DNA-Guided Endoribonuclease, Provides Insights Into Risc-Mediated mRNA Cleavage," *Molecular Cell* 19:405-419 (2005).

\* cited by examiner

Current Architecture:
Tail-to-Tail

Head-to-Tail Architecture

Head-to-Head Architecture

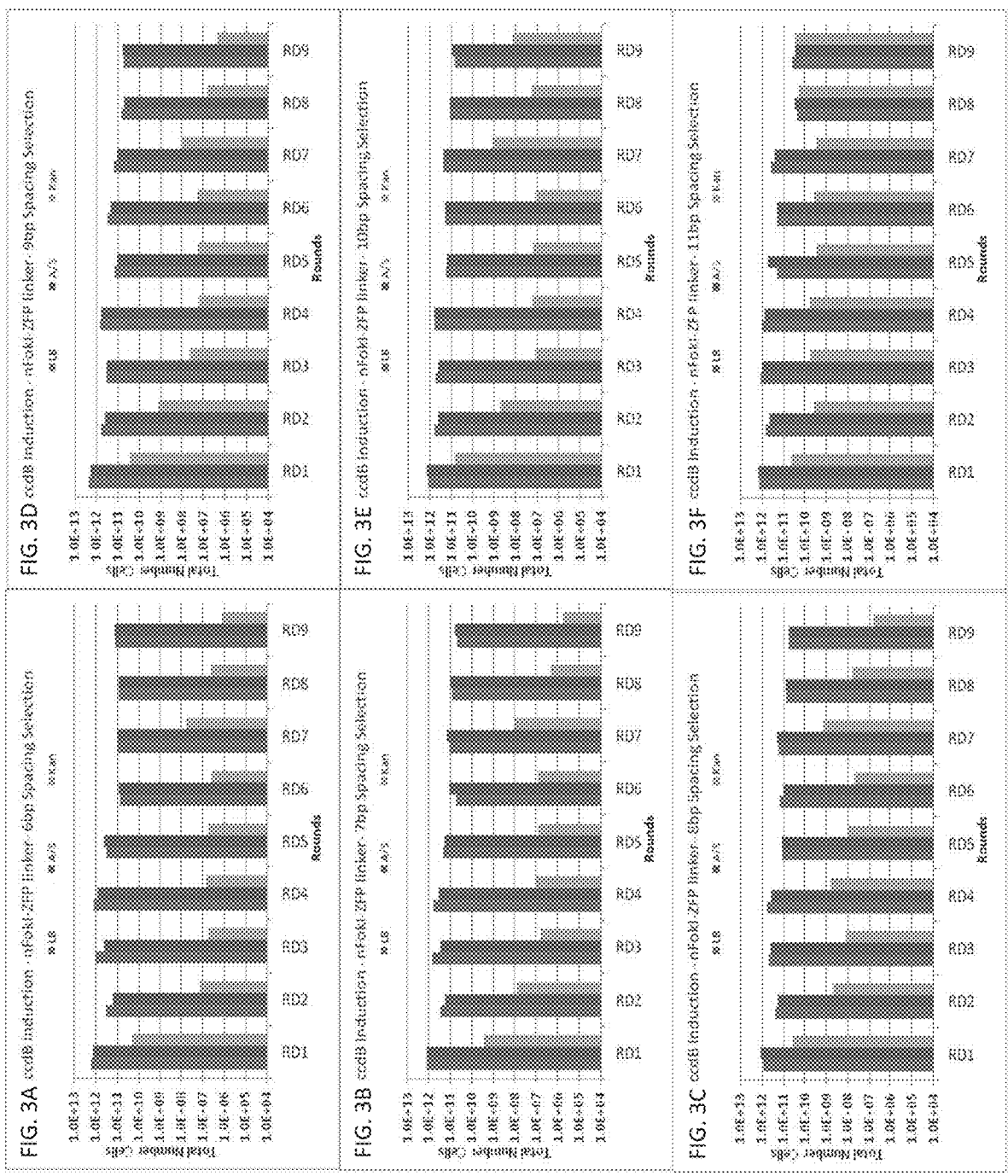

Figure 4

Linkers Selected for a 6bp Spacing

| Round 4 | Seq id | Round 6 | Seq id | Round 9 | Seq id |
|---|---|---|---|---|---|
| SGVFSTMTHD | 6 | SGISSVWS | 34 | SGMPAMPYGL | 59 |
| STVPNAQRELIY | 7 | FKPWYDEHVPLGAP | 35 | SGVEHSLYGA | 60 |
| SGLTDGCVHHYLDC | 8 | TGGTMWRPEY | 36 | SGNECSRFRP | 61 |
| SGIVQTWIPY | 9 | SPFPASVLDY | 37 | SGRSPEMDWC | 62 |
| AGAQSSQWDP | 10 | SGFDLTRGMLAQ | 38 | PNSYGLNPQLKT | 63 |
| SGTSSTRDLC | 11 | SGLHYDDLDL | 39 | SGVATRHVMG | 64 |
| AGRTGVTIDL | 12 | DPTFSKPYSP | 40 | SGVPSRDF | 65 |
| GPRGFKEYYD | 13 | SGCVSTIKAD | 41 | TGRPSPNYGV | 66 |
| SGSTARMVGS | 14 | SGKVRVSMFG | 42 | SGTKSSSDIC | 67 |
| SGQPCALQWV | 15 | CEAGERLPVWSE | 43 | SGSRFQHDFL | 68 |
| SGTYPDPLSD | 16 | TGNFNQGIVD | 44 | SGNIRVHPSY | 69 |
| SGLSSLDY | 17 | SGTPVNVGLY | 45 | VNNWGLSSLCPP | 70 |
| VADGTTTRNKSYETWC | 18 | SGELVQFIGH | 46 | SGQSPGDVGF | 71 |
| SATPSSRIEL | 19 | DSGIPRLSPP | 47 | GEAPNTPYAP | 72 |
| SGCKTAKPLL | 20 | SGDIPRYYVS | 48 | SGEVANAGLW | 73 |
| GGVTKGTWSD | 21 | SGVIKRVDTP | 49 | SGTRSSDLSC | 74 |
| SGSRTEIDVL | 22 | SGTYPLTFLH | 50 | DNPHFSYQRLRS | 75 |
| SGTRGMLHFP | 23 | SGNTVVYSVV | 51 | GYGPWSLTLPRFHG | 76 |
| TGGELSDTSYAL | 24 | SGRVGWRP | 52 | TGLPSKVYGA | 77 |
| SGAPSCSRSWLF | 25 | GSRMSKQPCWYP | 53 | SGSLRGVDPMWH | 78 |
| GAYSTTAFRP | 26 | SGIYTSESLI | 54 | SGTEPWRP | 79 |
| SGNILREVGYWS | 27 | SFSANFVVSKPYMG | 55 | GASLGPPWCP | 80 |
| SGTIKVFAQD | 28 | GDVASTFGENFY | 56 | SGLPMGSYGS | 81 |
| SERVMVRYEP | 29 | EEKGMLTSARSELV | 57 | SGAIYARPIE | 82 |
| EETPVRQYRP | 30 | SGTSTICEYH | 58 | SGAQGSTLDF | 83 |
| GQDMGLNRSSEWCA | 31 | | | SGVKRDSEII | 84 |
| GPPGDRRWAISS | 32 | | | SGLHYDDLDL | 39 |
| SGVMPLKLLD | 33 | | | | |

Figure 5    Linkers Selected for a 7bp Spacing

| Round 4 | Seq id | Round 6 | Seq id | Round 9 | Seq id |
|---|---|---|---|---|---|
| LACRPAQPPP | 85 | TGCKSVPRVGCI | 111 | SGVFSNPRCA | 135 |
| ARSDCPVYQLADNID | 86 | WDDPTDPIARSPAECL | 112 | SPGIRSSDPYIM | 136 |
| TGTTVLVSAL | 87 | EGAKRVEQLR | 113 | SGTKWIRSMA | 137 |
| SQATPTLYYTPL | 88 | SGERRQSHVL | 114 | SGFNHSSCDVVY | 138 |
| RTSGPPNTHRESTESN | 89 | LGAQPSKLVRSA | 115 | SGLVARTSDGFE | 139 |
| RAGCCAKSRVD | 90 | GVETAWVGSLVN | 116 | CISQGSYPIS | 140 |
| SGALQEPWSI | 91 | TQFRSPEVII | 117 | GGVKSVYPFI | 141 |
| SERVVMNSIG | 92 | RLLTHGASPPLL | 118 | SGHPLIVPSM | 142 |
| GMLRREVRQAELWE | 93 | SGRSVAAIGN | 119 | GPFRKPRNAAIH | 143 |
| IQPSQSQMGKRQMMVV | 94 | WLSGRTSAHAPDLY | 120 | SGMSSDLLHVTL | 144 |
| GGWKTLAKDWAW | 95 | YELSGNGTRSHEWPCS | 121 | QEQVSERDYHRMEY | 145 |
| ASGENLGPVRIPEKLA | 96 | GVVASEFGIDGPWS | 122 | SGSRIALTTN | 146 |
| SAPLMWQAYRRCPDVL | 97 | VTPARIDHMPIL | 123 | QSGKIASPHVVI | 147 |
| RMRPRMTKDSVD | 98 | LNMPSIQPEV | 124 | GSKRTASTWTVV | 148 |
| SMTVRKHLNAQKLC | 99 | GLHPVTSSVL | 125 | GGSQTNQVIR | 149 |
| SGAIRCHDEFWF | 100 | GFWSTAHKINFEES | 126 | TGRIVPKESV | 150 |
| TTEIDGALTQVPLH | 101 | TGSMVKCSVV | 127 | GPKNFDNEEFLH | 151 |
| QTMANPGFCSWVND | 102 | WGKPYSMGDY | 128 | SGAARTEDSY | 152 |
| ELADDNFARRQVIN | 103 | SGTLPFHYTC | 129 | TGLPHVRECV | 153 |
| TGARKTLLPEMF | 104 | SVRRMKQESREC | 130 | SGTPHEVGVYTL | 154 |
| EYLSRSRDYKDAFS | 105 | GGSRKRVGPFAAYE | 131 | NTNRSRVNLVIE | 155 |
| LGHAAGSAGRGTSV | 106 | SCRRLASDVAIS | 132 | SGLFSMPIAT | 156 |
| LGKTECTLYRTN | 107 | SGIVCSHSSA | 133 | FGESIFRPAP | 157 |
| QTGSMRQGTSLGHI | 108 | EQGDPRQGGHWSTSMH | 134 | GNTVSTSGIV | 158 |
| SGQPMFSWSD | 109 | | | TGTQSRSYAY | 159 |
| RLPALGSLSKYEPGVP | 110 | | | SGTFAVSGVS | 160 |
| | | | | GGRALSCMSRDKIV | 161 |

Linkers Selected for an 8bp Spacing

| Round 4 | SEQ | Round 6 | SEQ | Round 9 | SEQ |
|---|---|---|---|---|---|
| SGRTSSRVVSMLMSSG | 162 | TGRTYKRTSSVDSRCVDVRV | 190 | CAAGTWNVASTRDYE | 217 |
| VDSGTRLQGTLRKSENIL | 163 | SGNVCMMQRFKYRTPKHLIK | 191 | QWGNTPWRPVARQV | 218 |
| DENSRGVWAPKQVRC | 164 | TGTRTTAIRTPTGTSSSRTV | 192 | SGRVRMNTRSSSIE | 219 |
| SGRSTLVHSYLTARVM | 165 | SPDSTPKALANVRGLSSAMR | 193 | SGSSYKGTRPRPVK | 220 |
| SGGRMTHNIPWGKTSS | 166 | GHPLLTKQLACKRDIA | 194 | | |
| RPSGGSMSRAVQTMRRGLMSP | 167 | GGVQTRDSVKRSVM | 195 | | |
| SPVHSSSRGLFMRTVP | 168 | GGRSHALNTSVRQITPQY | 196 | | |
| SARAAPSTPGSRTRAV | 169 | DLLRKESSQPRRLQNVSV | 197 | | |
| SGNVLLRTSRSRKCGQHV | 170 | GATGHRDVRPRMVN | 198 | | |
| QRLAGDCSEPVVARGPKVID | 171 | GRVSDRSPVRKMAIQH | 199 | | |
| GSKGSKCVIKPFTNAS | 172 | GVSMGKCFVRDRTKVE | 200 | | |
| DDQPVRTAMAQPRNQVLL | 173 | SGKLGHQWCTIATPLK | 201 | | |
| GAFQCRKPGSISKPGVIT | 174 | SGAPMVCRTVRLSTQQ | 202 | | |
| GPGLRCPMYRSLDVSPTA | 175 | ESRLDMYLSAFRKVRNTEII | 203 | | |
| LESPEQNHTRVKKPVE | 176 | GSQTGQASRPHRDTTN | 204 | | |
| GQWKTRLGASTRQANNVVPK | 177 | TGSQPIVMRERATR | 205 | | |
| GTTAVRHYSSSSPN | 178 | LGDTNSTIRMSSSIKP | 206 | | |
| GGSRSPAVTRITRP | 179 | SGKRMKQLVQLVAT | 207 | | |
| FGSPWNGSFMRTSNVDSP | 180 | GAAQQSFRITSPSVSQIP | 208 | | |
| SGCLFQTSCVWVVP | 181 | SGRPSLKAGAKDAI | 209 | | |
| NGVRSVSPTYGDRYKQVA | 182 | ESRSDMNLSAFRKARNTEII | 210 | | |
| QPGWQSNPRWGTSHKEPL | 183 | SGGRWFKQVTRTSPSL | 211 | | |
| GQRLGPGHSMRTARTMPS | 184 | DGRLKVPWRTDYPSKA | 212 | | |
| SGSSRPKTYSFFPLTTPK | 185 | TGKTSDWFTGNPRLLS | 213 | | |
| SGRCRPKISRLSSV | 186 | GGVQRRCGYWAPTVIS | 214 | | |
| EGATRTRLWSPRPT | 187 | LGYPREDVHKRNMKHRPIVA | 215 | | |
| GDGKGPAQPKFVSDSV | 188 | SGGAASAILVDPVLVK | 216 | | |
| MERAlNNQTSRSSPQSNS | 189 | | | | |

Linkers Selected for a 9bp Spacing

| Round 4 | SEQ | Round 6 | SEQ | Round 9 | SEQ |
|---|---|---|---|---|---|
| KEFWARNY | 221 | KEFWARNY | 221 | SDAKPRNAARSKHALSFVGPRY | 225 |
| SGVFRPQRRSIRPRNNPGYSLP | 222 | QSFPGTVTNARRLADLCTFPRS | 226 | SEAKPRNAARSKHALSFVGPRY | 229 |
| QSNVTAPSTHRRPRKISNGVIP | 223 | SGVFRPQRRSIRPRNNPGYSLP | 222 | | |
| WGVRTEAVRSPLQARD | 224 | SDAKPRNAARSKHALSFVGPRY | 225 | | |
| SDAKPRNAARSKHALSFVGPRY | 225 | WGVKSHNARHGKHGGQ | 228 | | |
| QSFPGTVTNARRLADLCTFPRS | 226 | | | | |
| ATSLTPPFDVDVMR | 227 | | | | |

Linkers Selected for a 10bp Spacing

| Round 4 | Seq id | Round 6 | Seq id |
|---|---|---|---|
| DVRSTPPTDVLHDVYA | 230 | ARNVGMDVLGDVYM | 232 |
| ASEWLLDPKIYQHIAS | 231 | DVRSTPPTDVLHDVYA | 230 |
| ARNVGMDVLGDVYM | 232 | LAEDVERMDVLR | 241 |
| TTLYEVYR | 233 | TFGDLDDMLR | 247 |
| EWSMHQEVLN | 234 | EWSMHQEVLN | 234 |
| SSEDDVFS | 235 | QATLWEEELDEVLR | 248 |
| DPLEDVFR | 236 | ASEWLLDPKIYQHIAS | 231 |
| HMMSDVYK | 237 | DVRSTPPMDVLGDVYM | 249 |
| QSQSDIYA | 238 | AANDLPSRCDLQDIYT | 250 |
| TPLWDTYA | 239 | DKNPDDRSKKLDDVFQ | 243 |
| TRSPFWDPRLL | 240 | SGRPAPVLRGPSSRPSRRKPKV | 246 |
| LAEDVERMDVLR | 241 | | |
| EVRSTLPTDVLQDVYT | 242 | Round 9 | |
| DKNPDDRSKKLDDVFQ | 243 | SGRPAPVLRGPSSRPSRRKPKV | 246 |
| DSPYAVNDSNEDVEDVYR | 244 | SERRNTPSPMRREYTRNPSALP | 251 |
| NPQSAGAPSGHWLTTLLE | 245 | DVRSTPPTDVLHDVYA | 230 |
| SGRPAPVLRGPSSRPSRRKPKV | 246 | MVTSDPDILA | 252 |
| DVRSTPPTDVLHDVYA | 230 | SCLERALPFRKRYSRSPSTC | 253 |
| ASEWLLDPKIYQHIAS | 231 | | |
| ARNVGMDVLGDVYM | 232 | | |
| TTLYEVYR | 233 | | |
| EWSMHQEVLN | 234 | | |
| SSEDDVFS | 235 | | |
| DPLEDVFR | 236 | | |
| HMMSDVYK | 237 | | |
| QSQSDIYA | 238 | | |

Figure 8

Gap Profiling for Selected Linkers
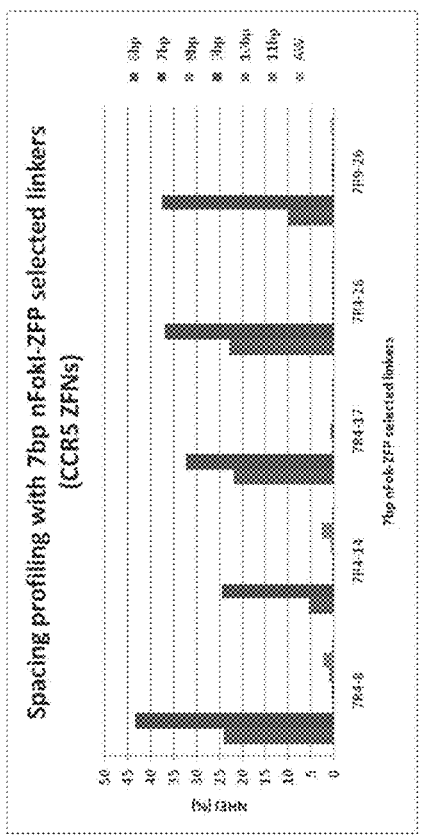
Figure 10A
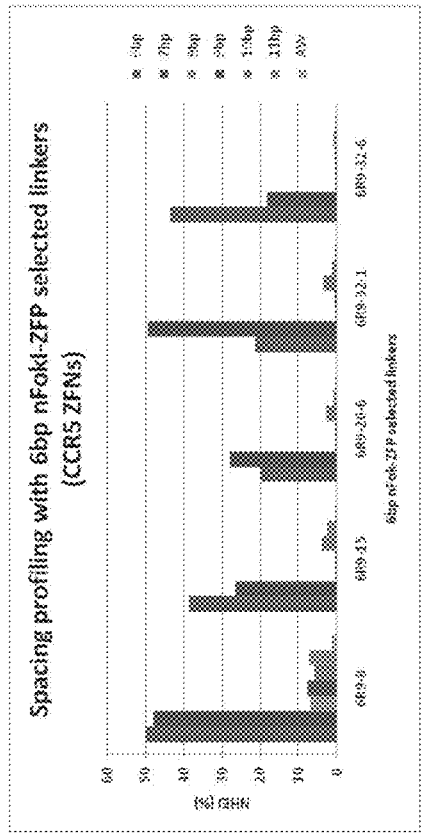
Figure 10B
Figure 10C
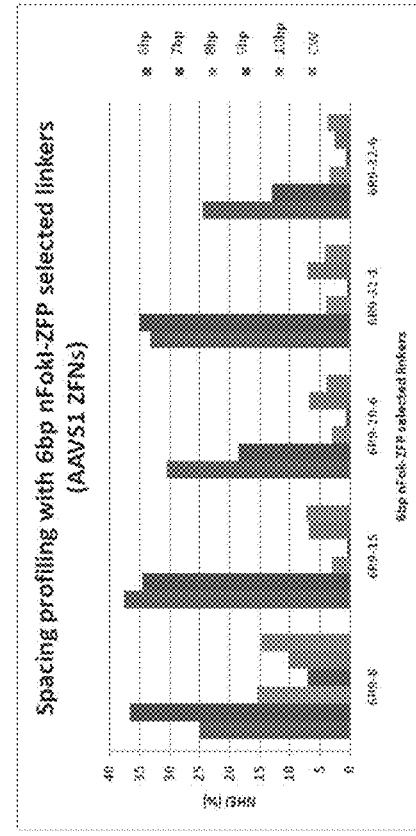
Figure 10D

Linkers Chosen for Portability Study

- 6 bp spacing
- 7 bp spacing

| | | Seq Id. | | | | Seq Id. |
|---|---|---|---|---|---|---|
| L1: | SGSLRGVDPMWH | 78 | | L1: | SQATPTLYYTPL | 88 |
| L2: | SGRSPEMDWC | 62 | | L2: | SGQPMFSWSD | 109 |
| L3: | GASLGPPWCP | 80 | | L3: | SGERRQSHVL | 114 |
| L4: | SGLPMGSYGS | 81 | | L4: | SGAIRCHDEFWF | 100 |
| L5: | SGQSPGDVGF | 71 | | L5: | SGALQEPWSI | 91 |
| L6: | SGAIYARPIE | 82 | | L6: | SGFNHSSCDVVY | 138 |
| L7: | SGAQGSTLDF | 83 | | L7: | QSGKIASPHVVI | 147 |
| L8: | SGVKRDSEII | 84 | | L8: | SGTPHEVGVYTL | 154 |

Experimental Setup for Portability Study

- CTLA4
  — ~450bp target window

| Architecture | Gap (bp) | # of targets | Linkers ZFN #1 | ZFN #2 | scale ZFNs | transfections |
|---|---|---|---|---|---|---|
| Head-to-tail | 6 | 10 | L0 | 6.1-6.8 | 90 | 80 |
| | 7 | 10 | L0 | 7.1-7.8 | 90 | 80 |
| | | | L7c5 | 6.1-6.8 | 90 | 80 |
| | 8 | 10 | L0 | 8.1-8.2 | 30 | 20 |
| | | | L7c5 | 6.1-6.3 | 40 | 30 |
| | | | | 7.1-7.2 | 20 | 20 |
| Tail-to-tail (standard) | 5 or 6 | 10 | L0 | L0 | 20 | 10 |
| | | | | | 380 | 320 |

Linkers Selected for a 6bp Spacing

Head-to-Tail 6bp Gap

| Pair | L1 | L2 | L3 | L4 | L5 | L6 | L7 | L8 | Cut site | Strand |
|---|---|---|---|---|---|---|---|---|---|---|
| 1 | 4.9 | 7.1 | 9.3 | 4.9 | 3.9 | 0.3 | 0.2 | 0.4 | 1220.5 | - |
| 2 | 0.1 | 0.2 | 0.3 | 0.2 | 0.6 | 1.1 | 0.7 | 0.1 | 1233.5 | - |
| 3 | 13.0 | 9.6 | 16.9 | 8.7 | 5.5 | 1.4 | 7.1 | 2.0 | 3809.5 | - |
| 4 | 0.9 | 2.3 | 5.7 | 2.0 | 0.1 | 1.5 | 5.8 | 3.1 | 3883.5 | + |
| 5 | 1.6 | 1.2 | 3.5 | 1.1 | 0.7 | 11.5 | 0.0 | 0.0 | 3924.5 | + |
| 6 | 0.2 | 0.1 | 0.1 | 52.9 | 63.7 | 2.3 | 64.7 | 58.4 | 3955.5 | + |
| 7 | 28.4 | 0.1 | 32.4 | 32.3 | 42.5 | 39.4 | 44.6 | 43.5 | 4035.5 | - |
| 8 | 0.2 | 0.2 | 0.2 | 0.1 | 0.2 | 0.2 | 0.2 | 0.1 | 4099.5 | - |
| 9 | 1.5 | 1.8 | 2.8 | 1.8 | 1.7 | 2.6 | 2.9 | 2.7 | 4116.5 | - |
| 10 | 0.3 | 0.5 | 0.5 | 0.5 | 0.3 | 0.9 | 0.7 | 0.3 | 4136.5 | + |
| average | 5.1 | 2.5 | 7.2 | 10.4 | 11.9 | 6.1 | 12.7 | 11.1 | | |

| LO Pairs | NHEJ | Cut site |
|---|---|---|
| 1 | 0.2 | 1262.5 |
| 2 | 10.5 | 3833.5 |
| 3 | 0.8 | 3859.5 |
| 4 | 15.0 | 3892 |
| 5 | 0.2 | 3966.5 |
| 6 | 0.3 | 4011 |
| 7 | 1.2 | 4077.5 |
| 8 | 21.7 | 4107 |
| 9 | 6.1 | 4115 |
| 10 | 0.1 | 4140 |
| average | 5.6 | | no DNA

Figure 13

Linkers Selected for a 7bp Spacing

Head-to-Tail 7bp Gap

| Pair | L1 | L2 | L3 | L4 | L5 | L6 | L7 | L8 | Cut site | Strand |
|---|---|---|---|---|---|---|---|---|---|---|
| 1 | 0.3 | 3.3 | 0.7 | 0.8 | 0.4 | 0.6 | 0.3 | 0.5 | 1226 | - |
| 2 | 0.4 | 0.4 | 0.4 | 0.6 | 0.3 | 0.6 | 0.4 | 0.3 | 1239 | - |
| 3 | 52.3 | 36.1 | 67.4 | 72.3 | 49.9 | 53.6 | 56.0 | 57.1 | 3829 | - |
| 4 | 19.9 | 27.1 | 26.5 | 26.0 | 22.2 | 29.7 | 27.9 | 39.2 | 3895 | - |
| 5 | 0.1 | 0.1 | 0.1 | 0.1 | 0.0 | 0.1 | 0.1 | 0.2 | 3916 | + |
| 6 | 8.1 | 9.0 | 9.3 | 13.6 | 8.7 | 6.8 | 7.3 | 11.6 | 3947 | + |
| 7 | 13.2 | 20.9 | 36.4 | 20.1 | 19.8 | 20.1 | 25.5 | 37.5 | 4074 | + |
| 8 | 0.4 | 1.6 | 1.6 | 2.0 | 0.6 | 1.3 | 0.4 | 3.9 | 4106 | + |
| 9 | 0.6 | 3.6 | 3.4 | 0.3 | 2.0 | 1.6 | 1.7 | 4.3 | 4110 | - |
| 10 | 0.2 | 0.2 | 0.3 | 0.1 | 0.2 | 0.2 | 0.2 | 0.1 | 4139 | + |
| average | 9.5 | 10.2 | 14.6 | 13.6 | 10.4 | 11.5 | 12.0 | 15.5 | | |

| LO Pairs | NHEJ | Cut site |
|---|---|---|
| 1 | 0.2 | 1262.5 |
| 2 | 18.2 | 3833.5 |
| 3 | 2.4 | 3859.5 |
| 4 | 29.3 | 3892 |
| 5 | 0.1 | 3966.5 |
| 6 | 0.3 | 4011 |
| 7 | 2.3 | 4077.5 |
| 8 | 36.3 | 4107 |
| 9 | 12.9 | 4115 |
| 10 | 0.2 | 4140 |
| average | 10.2 | |

Figure 14

Comparison of FokI Polarity in the Head-to-Tail Architecture (CTLA4)

| Pair | Linker | | Spacing | FokI Polarity ELD-KKR | KKR-ELD |
|---|---|---|---|---|---|
| 3 | L7: SGAQGSTLDF, | N6a | 6 | 6.1 | 13 |
| 3 | L5: SGQSPGDVGF, | N6b | 6 | 3.3 | 12.5 |
| 3 | L8: SGVKRDSEII, | N6c | 6 | 1.5 | 5.2 |
| 6 | L7: SGAQGSTLDF, | N6a | 6 | 35.8 | 59.5 |
| 6 | L5: SGQSPGDVGF, | N6b | 6 | 47.2 | 59.3 |
| 6 | L8: SGVKRDSEII, | N6c | 6 | 42.4 | 57.1 |
| 7 | L7: SGAQGSTLDF, | N6a | 6 | 27.2 | 50.6 |
| 7 | L5: SGQSPGDVGF, | N6b | 6 | 29.3 | 49.5 |
| 7 | L8: SGVKRDSEII, | N6c | 6 | 27.2 | 40.4 |
| 3 | L8: SGTPHEVGVYTL, | N7a | 7 | 54.6 | 58.7 |
| 3 | L3: SGERRQSHVL, | N7b | 7 | 43 | 41.1 |
| 3 | L4: SGAIRCHDEFWE, | N7c | 7 | 49.4 | 59.8 |
| 4 | L8: SGTPHEVGVYTL, | N7a | 7 | 17.3 | 22.8 |
| 4 | L3: SGERRQSHVL, | N7b | 7 | 27.6 | 33.7 |
| 4 | L4: SGAIRCHDEFWE, | N7c | 7 | 15.3 | 27.8 |
| 7 | L8: SGTPHEVGVYTL, | N7a | 7 | 15.4 | 15.2 |
| 7 | L3: SGERRQSHVL, | N7b | 7 | 16.7 | 8.1 |
| 7 | L4: SGAIRCHDEFWE, | N7c | 7 | 7.9 | 4.8 |

Figure 15

AAVS1 Set 22; Intron 1 Hypersensitive Site

Tail-to-Tail

| Pair | Linker L0 |
|---|---|
| 1 | 0.3 |
| 2 | 29.8 |
| 3 | 14.4 |
| 4 | 6.1 |
| 5 | 50.3 |
| 6 | 72.0 |
| 7 | 16.0 |
| 8 | |
| 9 | 65.3 |
| 10 | 70.3 |
| 11 | 4.5 |
| 12 | 36.6 |
| 13 | 49.3 |
| 14 | 8.9 |
| 15 | 15.9 |
| 16 | 43.7 |
| 17 | 57.7 |
| 18 | 0.6 |
| 19 | 3.4 |
| average | 30.3 | no dna

Head-to-Tail 6 bp gap

| Pair | Linker N6a | N6b | N6c |
|---|---|---|---|
| 1 | 3.7 | 1.5 | 3.9 |
| 2 | 1.1 | 1.3 | 0.8 |
| 3 | 2.1 | 1.1 | 1.3 |
| 4 | 1.1 | 1.4 | 0.7 |
| 5 | 49.3 | 24.6 | 56.7 |
| 6 | 36.2 | 24.6 | 29.8 |
| 7 | 8.6 | 2.1 | 7.3 |
| 8 | 64.3 | | 52.3 |
| 9 | 2.4 | 2.3 | 1.6 |
| 10 | 7.3 | 1.0 | 6.4 |
| 11 | 6.3 | 5.5 | 2.9 |
| 12 | 68.2 | 66.7 | 41.0 |
| 13 | 26.2 | 33.5 | 15.1 |
| 14 | 21.9 | 22.0 | 23.0 |
| 15 | 17.8 | 11.0 | 15.0 |
| 16 | 31.9 | 43.9 | 0.1 |
| 17 | 3.0 | 2.4 | 3.1 |
| 18 | 1.0 | 0.6 | 0.9 |
| 19 | 1.5 | 1.5 | 1.0 |
| average | 18.6 | 13.7 | 13.8 |

Head-to-Tail 7 bp gap

| Pair | Linker N7a | N7b | N7c |
|---|---|---|---|
| 1 | 21.2 | 27.9 | 15.5 |
| 2 | 9.2 | 11.4 | 11.5 |
| 3 | 5.8 | 5.4 | 4.7 |
| 4 | 5.8 | 2.1 | 4.8 |
| 5 | 46.0 | 48.6 | 51.2 |
| 6 | 30.0 | 26.5 | 27.0 |
| 7 | 0.2 | 0.2 | 0.4 |
| 8 | 27.8 | 12.9 | 23.0 |
| 9 | 0.4 | 0.5 | 0.2 |
| 10 | 24.1 | 8.5 | 15.3 |
| 11 | | | |
| 12 | 34.7 | 37.9 | 33.9 |
| 13 | 15.5 | 4.4 | 8.1 |
| 14 | 10.7 | 8.9 | 10.8 |
| 15 | 45.9 | 42.2 | 21.0 |
| 16 | 19.9 | 12.8 | 10.5 |
| 17 | 8.6 | 12.2 | 5.6 |
| 18 | 11.2 | 7.7 | 7.6 |
| 19 | 1.5 | 1.2 | 1.0 |
| average | 17.7 | 15.1 | 14.0 |

Figure 16

AAVS1 Set 23; Intron 1 Excluding Hypersensitive Site

| Tail-to-Tail | | | Head-to-Tail 6 bp gap | | | | | Head-to-Tail 7 bp gap | | | |
|---|---|---|---|---|---|---|---|---|---|---|---|
| | Linker | | | | Linker | | | | | Linker | |
| Pair | L0 | | Pair | N6a | N6b | N6c | | Pair | N7a | N7b | N7c |
| 1 | 1.7 | | 1 | 0.5 | 0.3 | 0.4 | | 1 | 35.6 | 9.4 | 17.9 |
| 2 | 0.1 | | 2 | 3.9 | 8.3 | 3.9 | | 2 | 26.0 | 27.1 | 28.0 |
| 3 | 25.8 | | 3 | 4.2 | 1.1 | 3.4 | | 3 | 0.7 | 0.1 | 0.2 |
| 4 | 15.7 | | 4 | 11.9 | 6.7 | 8.4 | | 4 | 0.2 | 0.1 | 0.1 |
| 5 | 14.8 | | 5 | 8.8 | 8.3 | 2.6 | | 5 | 6.2 | 2.8 | 2.2 |
| 6 | 13.4 | | 6 | 0.3 | 0.1 | 0.3 | | 6 | 41.2 | 53.7 | 50.2 |
| 7 | 34.1 | | 7 | 35.4 | 28.2 | 37.2 | | 7 | | | |
| 8 | 1.8 | | 8 | 0.9 | 0.7 | 0.8 | | 8 | | | |
| 9 | 12.2 | | 9 | 28.5 | 20.0 | 24.0 | | 9 | 23.2 | 27.0 | 16.4 |
| 10 | | | 10 | 5.6 | 3.0 | 3.7 | | 10 | 3.6 | 4.9 | 3.2 |
| 11 | 48.1 | | 11 | 18.0 | 10.4 | 19.2 | | 11 | 62.8 | 66.8 | 60.7 |
| 12 | 13.8 | | 12 | 90.5 | 89.6 | 89.0 | | 12 | 4.2 | 2.5 | 1.4 |
| 13 | 5.8 | | 13 | 1.3 | 1.5 | 1.2 | | 13 | 5.7 | 5.0 | 7.6 |
| 14 | 11.2 | | 14 | 8.1 | 6.4 | 12.4 | | 14 | 0.4 | 0.7 | 2.5 |
| 15 | 1.0 | | 15 | 17.4 | 9.7 | 13.0 | | 15 | | | |
| 16 | 9.7 | | 16 | 0.7 | 0.7 | 0.7 | | 16 | 2.5 | 1.9 | 1.1 |
| 17 | 5.8 | | 17 | 10.8 | 6.6 | 4.9 | | 17 | 0.4 | 0.3 | 0.2 |
| 18 | 8.0 | | 18 | 13.3 | 6.0 | 8.4 | | 18 | 19.9 | 16.7 | 20.7 |
| 19 | 49.8 | | 19 | 37.3 | 28.3 | 36.5 | | 19 | | | |
| average | 15.1 | | average | 15.7 | 12.4 | 14.2 | | average | 15.5 | 14.6 | 14.2 | no dna

Head-to-Head Architecture Screen; AAVS1 Intron 1

5bp spacing

| Pair # | Linker N6a | N6b | N7a | N7b |
|---|---|---|---|---|
| 1 | 0.1 | 0.2 | 0.1 | 1.2 |
| 2 | 2.4 | 2.5 | 0.5 | 0.3 |
| 3 | 0.2 | 0.4 | 1.9 | 1.7 |
| 4 | | | 6.9 | 0.7 |
| 5 | | | | 0.3 |
| 6 | 0.9 | 0.2 | 1.7 | 0.4 |
| 7 | 0.4 | 0.5 | 1.0 | 0.4 |
| 8 | 0.2 | 0.2 | 0.5 | 0.4 |
| 9 | 0.6 | 0.5 | 10.7 | 3.0 |
| 10 | 0.4 | 0.3 | 0.1 | 0.1 |
| 11 | 0.8 | 0.3 | 0.2 | 0.3 |

6bp spacing

| Pair # | Linker N6a | N6b | N7a | N7b |
|---|---|---|---|---|
| 1 | 1.5 | 1.4 | 2.2 | 1.2 |
| 2 | 0.5 | 0.7 | 0.5 | 0.3 |
| 3 | 2.9 | 1.2 | 1.9 | 1.7 |
| 4 | 0.1 | 0.4 | 6.9 | 0.7 |
| 5 | 0.4 | 0.3 | | 0.3 |
| 6 | 0.8 | 0.4 | 1.7 | 0.4 |
| 7 | 0.4 | 0.4 | 1.0 | 0.4 |
| 8 | 0.4 | 0.4 | 0.5 | 0.4 |
| 9 | 3.2 | 0.5 | 10.7 | 3.0 |
| 10 | 0.1 | 0.1 | 0.1 | 0.1 |
| 11 | 0.2 | 0.2 | 0.2 | 0.3 |

Legend:
- Shaded: Low total # sequences
- Primer problem
- empty: no sequences found

- N6a: SGAQGSTLDF
- N6b: SGQSPGDVGF
- N7a: SGTPREVGVYTL
- N7b: SGERRQSHVL

7bp spacing

| Pair # | Linker N6a | N6b | N7a | N7b |
|---|---|---|---|---|
| 1 | 0.1 | 4.9 | 0.1 | 0.7 |
| 2 | | | | |
| 3 | 1.6 | 0.5 | 3.9 | 1.1 |
| 4 | 11.5 | 7.9 | 5.4 | 3.1 |
| 5 | 16.5 | 5.4 | 4.1 | 1.2 |
| 6 | | | 0.2 | 12.6 |
| 7 | | | | |
| 8 | 12.6 | 5.0 | 4.5 | 4.4 |
| 9 | 73.6 | 76.2 | 60.4 | 39.9 |
| 10 | 21.2 | 0.5 | 0.4 | 0.8 |
| 11 | 1.2 | 0.7 | 0.6 | 0.4 |

8bp spacing

| Pair # | Linker N6a | N6b | N7a | N7b |
|---|---|---|---|---|
| 1 | | | | |
| 2 | 19.4 | 4.8 | 13.5 | 5.3 |
| 3 | 1.0 | 1.1 | 99.3 | 1.0 |
| 4 | 18.2 | 18.1 | 23.2 | 17.8 |
| 5 | 70.9 | 71.7 | 41.5 | 65.0 |
| 6 | 0.8 | 0.6 | 0.8 | 0.3 |
| 7 | | | | |
| 8 | 76.6 | 61.9 | 79.5 | 0.5 |
| 9 | 47.6 | 14.5 | 69.4 | 43.6 |
| 10 | 0.4 | 0.7 | 2.2 | 0.5 |
| 11 | 57.1 | 15.9 | 56.8 | 21.8 |

9bp spacing

| Pair # | Linker N7a | N7b |
|---|---|---|
| 1 | 44.1 | 1.3 |
| 2 | 5.9 | 2.3 |
| 3 | 2.9 | 2.3 |
| 4 | 75.8 | 2.8 |
| 5 | 0.3 | 0.2 |
| 6 | 27.4 | 0.9 |
| 7 | | |
| 8 | 23.4 | 10.1 |
| 9 | 13.3 | 9.2 |
| 10 | 0.1 | 0.6 |
| 11 | 0.4 | 0.3 |

Figure 18

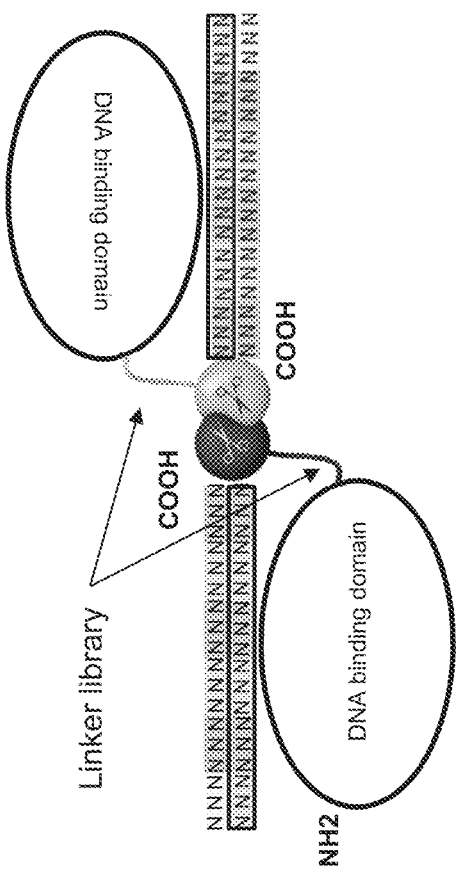 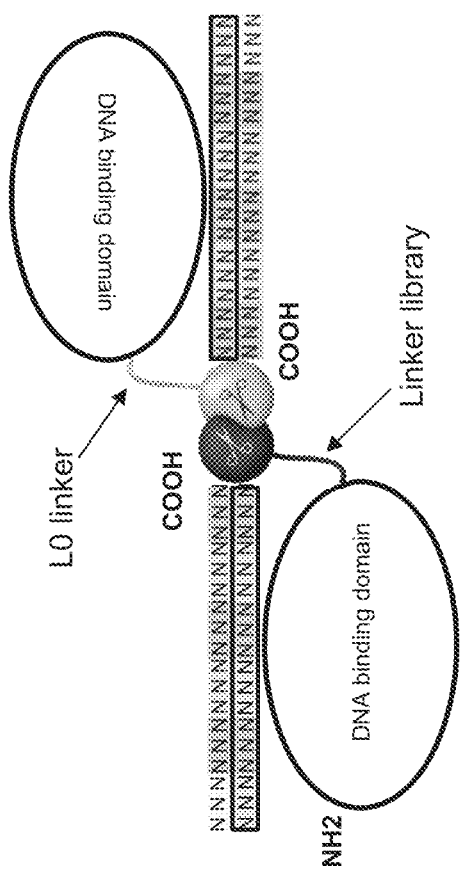
Figure 19A

Figure 19B

ASYMMETRIC LINKERS

7bp gap

| | SEQ ID | Activity in CCR5 cells |
|---|---|---|
| MGDEHRKLRLMSQMRLQVD | 254 | 36.0 |
| KPRTDRKIFSLRLAN | 255 | 33.5 |
| NPLPRNKYPSPYFLH | 266 | 30.7 |
| APPAASKSRTWEMRR | 267 | 28.0 |
| LNRPKLNTRPHYTSV | 268 | 27.9 |
| QTRPPRSFCMLAMTG | 269 | 27.6 |

8bp gap

| | SEQ ID | |
|---|---|---|
| MHGPRLPPLKLCGAWSIG | 270 | 47.3 |
| GPRVVTRRVLATVTVA | 271 | 43.5 |
| LGMVSRPRLNQRAPIPKS | 272 | 42.5 |
| QYPRHPTTSKRIGPTDRVLT | 273 | 42.3 |
| YPREATSRRETDILNSKRLLS | 274 | 42.1 |
| QCNPVLKCRTIKPGPSAA | 275 | 41.0 |

9bp gap

| | SEQ ID | |
|---|---|---|
| QPTWMKSPRKKRYPTGRLTAQ | 276 | 42.5 |
| DPEYLSQRVPRRRQKPPMTRPY | 277 | 37.8 |
| MEQRVRATNPRRLAILTTESFM | 278 | 36.1 |
| QSPNMIQRTPKRRTPLTIPLR | 279 | 28.5 |

SYMMETRIC LINKERS

9bp gap

| | SEQ ID | Activity in CCR5 cells |
|---|---|---|
| AGNCARLTVRPPFSHP | 280 | 32.2 |
| ERPPRSLASPPHALLL | 281 | 31.6 |

Controls

| Cell line | Activity of AAVS1 ZFNs |
|---|---|
| 7bp gap cell line | 38.1 |
| 8bp gap cell line | 23.4 |
| 9bp gap cell line | 37.7 |

SEQUENCE LISTING

```
<160> NUMBER OF SEQ ID NOS: 286

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Asn Gly Glu Ile Asn Phe
1               5

<210> SEQ ID NO 2
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 2

Glu Arg Pro Phe Gln Cys Arg Ile Cys Met Arg Asn Phe Ser Arg Ser
1               5                   10                  15

Asp Asn Leu Gly Val His Ile Arg Thr His Thr Gly Glu
            20                  25

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Pro Phe Ala Cys Asp Ile Cys Gly Arg Lys Phe Ala Gln Lys Ile
1               5                   10                  15

Asn Leu Gln Val His Thr Lys Ile His Thr Gly Glu
            20                  25

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Pro Phe Gln Cys Arg Ile Cys Met Arg Asn Phe Ser Arg Ser Asp
1               5                   10                  15

Val Leu Ser Glu His Ile Arg Thr His Thr Gly Glu
            20                  25

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Lys Pro Phe Ala Cys Asp Ile Cys Gly Arg Lys Phe Ala Gln Arg Asn
1               5                   10                  15

His Arg Thr Thr His Thr Lys Ile His Leu Arg Gln Lys Asp
            20                  25                  30

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gly Val Phe Ser Thr Met Thr His Asp
1               5                   10

<210> SEQ ID NO 7
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Thr Val Pro Asn Ala Gln Arg Glu Leu Ile Tyr
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gly Leu Thr Asp Gly Cys Val His His Tyr Leu Asp Cys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Gly Ile Val Gln Thr Trp Ile Pro Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Gly Ala Gln Ser Ser Gln Trp Asp Pro
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gly Thr Ser Ser Thr Arg Asp Leu Cys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

Ala Gly Arg Thr Gly Val Thr Ile Asp Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Pro Arg Gly Phe Lys Glu Tyr Tyr Asp
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly Ser Thr Ala Arg Met Val Gly Ser
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Gly Gln Pro Cys Ala Leu Gln Trp Val
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gly Thr Tyr Pro Asp Pro Leu Ser Asp
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Gly Leu Ser Ser Leu Asp Tyr
1               5

<210> SEQ ID NO 18
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 18

Val Ala Asp Gly Thr Thr Thr Arg Asn Lys Ser Tyr Glu Thr Trp Cys
1               5                   10                  15

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ala Thr Pro Ser Ser Arg Ile Glu Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Gly Cys Lys Thr Ala Lys Pro Leu Leu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Val Thr Lys Gly Thr Trp Ser Asp
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Gly Ser Arg Thr Glu Ile Asp Val Leu
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gly Thr Arg Gly Met Leu His Phe Pro
1               5                   10
```

```
<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Gly Gly Glu Leu Ser Asp Thr Ser Tyr Ala Leu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Gly Ala Pro Ser Cys Ser Arg Ser Trp Leu Phe
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ala Tyr Ser Thr Thr Ala Phe Arg Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Gly Asn Ile Leu Arg Glu Val Gly Tyr Trp Ser
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Gly Thr Ile Lys Val Phe Ala Gln Asp
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29
```

Ser Glu Arg Val Met Val Arg Tyr Glu Pro
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Glu Thr Pro Val Arg Gln Tyr Arg Pro
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gln Asp Met Gly Leu Asn Arg Ser Ser Glu Trp Cys Ala
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Pro Pro Gly Asp Arg Arg Trp Ala Ile Ser Ser
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Gly Val Met Pro Leu Lys Leu Leu Asp
1               5                   10

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Gly Ile Ser Ser Val Trp Ser
1               5

<210> SEQ ID NO 35
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 35

Phe Lys Pro Trp Tyr Asp Glu His Val Pro Leu Gly Ala Pro
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Gly Gly Thr Met Trp Arg Pro Glu Tyr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Pro Phe Pro Ala Ser Val Leu Asp Tyr
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Gly Phe Asp Leu Thr Arg Gly Met Leu Ala Gln
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Gly Leu His Tyr Asp Asp Leu Asp Leu
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Pro Thr Phe Ser Lys Pro Tyr Ser Pro
1               5                   10
```

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Gly Cys Val Ser Thr Ile Lys Ala Asp
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Gly Lys Val Arg Val Ser Met Phe Gly
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Glu Ala Gly Glu Arg Leu Pro Val Trp Ser Glu
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Gly Asn Phe Asn Gln Gly Ile Val Asp
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Gly Thr Pro Val Asn Val Gly Leu Tyr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Gly Glu Leu Val Gln Phe Ile Gly His
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Ser Gly Ile Pro Arg Leu Ser Pro Pro
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Gly Asp Ile Pro Arg Tyr Tyr Val Ser
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Gly Val Ile Lys Arg Val Asp Thr Pro
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Gly Thr Tyr Pro Leu Thr Phe Leu His
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Gly Asn Thr Val Val Tyr Ser Val Val
1               5                   10

<210> SEQ ID NO 52
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 52

Ser Gly Arg Val Gly Trp Arg Pro
1               5

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ser Arg Met Ser Lys Gln Pro Cys Trp Tyr Pro
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Gly Ile Tyr Thr Ser Glu Ser Leu Ile
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Phe Ser Ala Asn Phe Val Val Ser Lys Pro Tyr Met Gly
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Asp Val Ala Ser Thr Phe Gly Glu Asn Phe Tyr
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Glu Lys Gly Met Leu Thr Ser Ala Arg Ser Glu Leu Val
1               5                   10
```

-continued

```
<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Gly Thr Ser Thr Ile Cys Glu Tyr His
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Gly Met Pro Ala Met Pro Tyr Gly Leu
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Gly Val Glu His Ser Leu Tyr Gly Ala
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Gly Asn Glu Cys Ser Arg Phe Arg Pro
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Gly Arg Ser Pro Glu Met Asp Trp Cys
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 63

Pro Asn Ser Tyr Gly Leu Asn Pro Gln Leu Lys Thr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Gly Val Ala Thr Arg His Val Met Gly
1               5                   10

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Gly Val Pro Ser Arg Asp Phe
1               5

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Gly Arg Pro Ser Pro Asn Tyr Gly Val
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Gly Thr Lys Ser Ser Ser Asp Ile Cys
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Gly Ser Arg Phe Gln His Asp Phe Leu
1               5                   10

<210> SEQ ID NO 69
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Gly Asn Ile Arg Val His Pro Ser Tyr
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Val Asn Asn Trp Gly Leu Ser Ser Leu Cys Pro Pro
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Gly Gln Ser Pro Gly Asp Val Gly Phe
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Glu Ala Pro Asn Thr Pro Tyr Ala Pro
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Gly Glu Val Ala Asn Ala Gly Leu Trp
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Gly Thr Arg Ser Ser Asp Leu Ser Cys
```

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Asn Pro His Phe Ser Tyr Gln Arg Leu Arg Ser
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Tyr Gly Pro Trp Ser Leu Thr Leu Pro Arg Phe His Gly
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Gly Leu Pro Ser Lys Val Tyr Gly Ala
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Gly Ser Leu Arg Gly Val Asp Pro Met Trp His
1               5                   10

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Gly Thr Glu Pro Trp Arg Pro
1               5

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 80

Gly Ala Ser Leu Gly Pro Pro Trp Cys Pro
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Gly Leu Pro Met Gly Ser Tyr Gly Ser
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Gly Ala Ile Tyr Ala Arg Pro Ile Glu
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser Gly Ala Gln Gly Ser Thr Leu Asp Phe
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Gly Val Lys Arg Asp Ser Glu Ile Ile
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Ala Cys Arg Pro Ala Gln Pro Pro Pro
1               5                   10

<210> SEQ ID NO 86

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Arg Ser Asp Cys Pro Val Tyr Val Gln Leu Ala Asp Asn Ile Asp
1               5                   10                  15

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Gly Thr Thr Val Leu Val Ser Ala Leu
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Gln Ala Thr Pro Thr Leu Tyr Tyr Thr Pro Leu
1               5                   10

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Thr Ser Gly Pro Pro Asn Thr His Arg Glu Ser Ile Glu Ser Asn
1               5                   10                  15

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Ala Gly Cys Ala Lys Ser Arg Val Asp
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91
```

Ser Gly Ala Leu Gln Glu Pro Trp Ser Ile
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Glu Arg Val Val Met Asn Ser Ile Gly
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Met Leu Arg Arg Glu Val Arg Gln Ala Glu Leu Trp Glu
1               5                   10

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ile Gln Pro Ser Gln Ser Gln Met Gly Lys Arg Gln Met Met Val Val
1               5                   10                  15

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly Trp Lys Thr Leu Ala Lys Asp Trp Ala Trp
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Ser Gly Glu Asn Leu Gly Pro Val Arg Ile Pro Glu Lys Leu Ala
1               5                   10                  15

<210> SEQ ID NO 97
<211> LENGTH: 16
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 97

Ser Ala Pro Leu Met Trp Gln Ala Tyr Arg Arg Cys Pro Asp Val Leu
1               5                   10                  15

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Met Arg Pro Arg Met Thr Lys Asp Ser Val Asp
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Met Thr Val Arg Lys His Leu Asn Ala Gln Lys Leu Cys
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Gly Ala Ile Arg Cys His Asp Glu Phe Trp Phe
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Thr Glu Ile Asp Gly Ala Leu Thr Gln Val Pro Leu His
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gln Thr Met Ala Asn Pro Gly Phe Cys Ser Trp Val Asn Asp
1               5                   10

```
<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Glu Leu Ala Asp Asp Asn Phe Ala Arg Arg Gln Val Ile Asn
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Thr Gly Ala Arg Lys Thr Leu Leu Pro Glu Met Phe
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Glu Tyr Leu Ser Arg Ser Arg Asp Tyr Lys Asp Ala Phe Ser
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Leu Gly His Ala Ala Gly Ser Ala Gly Arg Gly Thr Ser Val
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Gly Lys Thr Glu Cys Thr Leu Tyr Arg Thr Asn
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108
```

```
Gln Thr Gly Ser Met Arg Gln Gly Thr Ser Leu Gly His Ile
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Gly Gln Pro Met Phe Ser Trp Ser Asp
1               5                   10

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Leu Pro Ala Leu Gly Ser Leu Ser Lys Tyr Glu Pro Gly Val Pro
1               5                   10                  15

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Gly Cys Lys Ser Val Pro Arg Val Gly Cys Ile
1               5                   10

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Trp Asp Asp Pro Thr Asp Pro Ile Ala Arg Ser Pro Ala Glu Cys Leu
1               5                   10                  15

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Glu Gly Ala Lys Arg Val Glu Gln Leu Arg
1               5                   10

<210> SEQ ID NO 114
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 114

Ser Gly Glu Arg Arg Gln Ser His Val Leu
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Leu Gly Ala Gln Pro Ser Lys Leu Val Arg Ser Ala
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Val Glu Thr Ala Trp Val Gly Ser Leu Val Asn
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Thr Gln Phe Arg Ser Pro Glu Val Ile Ile
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Leu Leu Thr His Gly Ala Ser Pro Pro Leu Leu
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Gly Arg Ser Val Ala Ala Ile Gly Asn
1               5                   10
```

```
<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Trp Leu Ser Gly Arg Thr Ser Ala His Ala Pro Asp Leu Tyr
1               5                   10

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Tyr Glu Leu Ser Gly Asn Gly Thr Arg Ser His Glu Trp Pro Cys Ser
1               5                   10                  15

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Val Val Ala Ser Glu Phe Gly Ile Asp Gly Pro Trp Ser
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Val Thr Pro Ala Arg Ile Asp His Met Pro Ile Leu
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Leu Asn Met Pro Ser Ile Gln Pro Glu Val
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 125

Gly Leu His Pro Val Thr Ser Ser Val Leu
1               5                   10

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Phe Trp Ser Thr Ala His Lys Ile Asn Phe Glu Glu Ser
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Thr Gly Ser Met Val Lys Cys Ser Val Val
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Trp Gly Lys Pro Tyr Ser Met Gly Asp Tyr
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Gly Thr Leu Pro Phe His Tyr Thr Cys
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ser Val Arg Arg Met Lys Gln Glu Ser Arg Glu Cys
1               5                   10

<210> SEQ ID NO 131
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 131

Gly Gly Ser Arg Lys Arg Val Gly Pro Phe Ala Ala Tyr Glu
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Cys Arg Arg Leu Ala Ser Asp Val Ala Ile Ser
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Gly Ile Val Cys Ser His Ser Ser Ala
1               5                   10

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Glu Gln Gly Asp Pro Arg Gln Gly Gly His Trp Ser Thr Ser Met His
1               5                   10                  15

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ser Gly Val Phe Ser Asn Pro Arg Cys Ala
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Pro Gly Ile Arg Ser Ser Asp Pro Tyr Ile Met
1               5                   10
```

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Gly Thr Lys Trp Ile Arg Ser Met Ala
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Gly Phe Asn His Ser Ser Cys Asp Val Val Tyr
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Gly Leu Val Ala Arg Thr Ser Asp Gly Phe Glu
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Ile Ser Gln Gly Ser Tyr Pro Ile Ser
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Gly Val Lys Ser Val Tyr Pro Phe Ile
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 142

Ser Gly His Pro Leu Ile Val Pro Ser Met
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Pro Phe Arg Lys Pro Arg Asn Ala Ala Ile His
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ser Gly Met Ser Ser Asp Leu Leu His Val Thr Leu
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Glu Gln Val Ser Glu Arg Asp Tyr His Arg Met Glu Tyr
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Gly Ser Arg Ile Ala Leu Thr Thr Asn
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gln Ser Gly Lys Ile Ala Ser Pro His Val Val Ile
1               5                   10

<210> SEQ ID NO 148
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Ser Lys Arg Thr Ala Ser Thr Trp Thr Val Val
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Gly Ser Gln Thr Asn Gln Val Ile Arg
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Thr Gly Arg Ile Val Pro Lys Glu Ser Val
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Pro Lys Asn Phe Asp Asn Glu Glu Phe Leu His
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ser Gly Ala Ala Arg Thr Glu Asp Ser Tyr
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Thr Gly Leu Pro His Val Arg Glu Cys Val
```

```
1               5                   10
```

```
<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Gly Thr Pro His Glu Val Gly Val Tyr Thr Leu
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asn Thr Asn Arg Ser Arg Val Asn Leu Val Ile Glu
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ser Gly Leu Phe Ser Met Pro Ile Ala Thr
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Phe Gly Glu Ser Ile Phe Arg Pro Ala Pro
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Asn Thr Val Ser Thr Ser Gly Ile Val
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 159

Thr Gly Thr Gln Ser Arg Ser Tyr Ala Tyr
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Gly Thr Phe Ala Val Ser Gly Val Ser
1               5                   10

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Gly Arg Ala Leu Ser Cys Met Ser Arg Asp Lys Ile Val
1               5                   10

<210> SEQ ID NO 162
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Gly Arg Thr Ser Ser Arg Val Val Ser Met Leu Met Ser Ser Gly
1               5                   10                  15

<210> SEQ ID NO 163
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Val Asp Ser Gly Thr Arg Leu Gln Gly Thr Leu Arg Lys Ser Glu Asn
1               5                   10                  15

Ile Leu

<210> SEQ ID NO 164
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asp Glu Asn Ser Arg Gly Val Val Trp Ala Pro Lys Gln Val Arg Cys
1               5                   10                  15

```
<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Gly Arg Ser Thr Leu Val His Ser Tyr Leu Thr Ala Arg Val Met
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ser Gly Gly Arg Met Thr His Asn Ile Pro Trp Gly Lys Thr Ser Ser
1               5                   10                  15

<210> SEQ ID NO 167
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Pro Ser Gly Ser Met Ser Arg Ala Val Gln Thr Met Arg Arg Gly
1               5                   10                  15

Leu Met Ser Pro
            20

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ser Pro Val His Ser Ser Ser Arg Gly Leu Phe Met Arg Thr Val Pro
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ser Ala Arg Ala Ala Pro Ser Thr Pro Gly Ser Arg Thr Arg Ala Val
1               5                   10                  15

<210> SEQ ID NO 170
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 170

Ser Gly Asn Val Leu Leu Arg Thr Ser Arg Ser Arg Lys Cys Gly Gln
1               5                   10                  15

His Val

<210> SEQ ID NO 171
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gln Arg Leu Ala Gly Asp Cys Ser Glu Pro Val Val Ala Arg Gly Pro
1               5                   10                  15

Lys Val Ile Asp
            20

<210> SEQ ID NO 172
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Ser Lys Gly Ser Lys Cys Val Ile Lys Pro Phe Thr Asn Ala Ser
1               5                   10                  15

<210> SEQ ID NO 173
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Asp Asp Gln Pro Val Arg Thr Ala Met Ala Gln Pro Arg Asn Gln Val
1               5                   10                  15

Leu Leu

<210> SEQ ID NO 174
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Ala Phe Gln Cys Arg Lys Pro Gly Ser Ile Ser Lys Pro Gly Val
1               5                   10                  15

Ile Thr

<210> SEQ ID NO 175
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 175

Gly Pro Gly Leu Arg Cys Pro Met Tyr Arg Ser Leu Asp Val Ser Pro
1               5                   10                  15

Thr Ala

<210> SEQ ID NO 176
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Leu Glu Ser Pro Glu Gln Asn His Thr Arg Val Lys Lys Pro Val Glu
1               5                   10                  15

<210> SEQ ID NO 177
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Gln Trp Lys Thr Arg Leu Gly Ala Ser Thr Arg Gln Ala Asn Asn
1               5                   10                  15

Val Val Pro Lys
            20

<210> SEQ ID NO 178
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Thr Thr Ala Val Arg His Tyr Ser Ser Ser Ser Pro Asn
1               5                   10

<210> SEQ ID NO 179
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Gly Ser Arg Ser Pro Ala Val Thr Arg Ile Thr Arg Pro
1               5                   10

<210> SEQ ID NO 180
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180
```

```
Phe Gly Ser Pro Trp Asn Gly Ser Phe Met Arg Thr Ser Asn Val Asp
1               5                   10                  15

Ser Pro
```

<210> SEQ ID NO 181
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

```
Ser Gly Cys Leu Pro Gln Thr Ser Cys Val Trp Val Val Pro
1               5                   10
```

<210> SEQ ID NO 182
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

```
Asn Gly Val Arg Ser Val Ser Pro Thr Tyr Gly Asp Arg Tyr Lys Gln
1               5                   10                  15

Val Ala
```

<210> SEQ ID NO 183
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

```
Gln Pro Gly Trp Gln Ser Asn Pro Arg Trp Gly Thr Ser His Lys Glu
1               5                   10                  15

Pro Leu
```

<210> SEQ ID NO 184
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
Gly Gln Arg Leu Gly Pro Gly His Ser Met Arg Thr Ala Arg Thr Met
1               5                   10                  15

Pro Ser
```

<210> SEQ ID NO 185
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

```
Ser Gly Ser Ser Arg Pro Lys Thr Tyr Ser Phe Phe Pro Leu Thr Thr
1               5                   10                  15

Pro Lys

<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser Gly Arg Cys Arg Pro Lys Ile Ser Arg Leu Ser Ser Val
1               5                   10

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Glu Gly Ala Thr Arg Thr Arg Leu Trp Ser Pro Arg Pro Thr
1               5                   10

<210> SEQ ID NO 188
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Asp Gly Lys Gly Pro Ala Gln Pro Lys Phe Val Ser Asp Ser Val
1               5                   10                  15

<210> SEQ ID NO 189
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Met Glu Arg Ala Leu Asn Asn Gln Thr Ser Arg Ser Ser Pro Gln Ser
1               5                   10                  15

Asn Ser

<210> SEQ ID NO 190
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Thr Gly Arg Thr Tyr Lys Arg Thr Ser Ser Val Asp Ser Arg Cys Val
1               5                   10                  15

Asp Val Arg Val
            20
```

<210> SEQ ID NO 191
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Gly Asn Val Cys Met Met Gln Arg Phe Lys Tyr Arg Thr Pro Lys
1               5                   10                  15

His Leu Ile Lys
            20

<210> SEQ ID NO 192
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Thr Gly Thr Arg Thr Thr Ala Ile Arg Thr Pro Thr Gly Thr Ser Ser
1               5                   10                  15

Ser Arg Thr Val
            20

<210> SEQ ID NO 193
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Pro Asp Ser Thr Pro Lys Ala Leu Ala Asn Val Arg Gly Leu Ser
1               5                   10                  15

Ser Ala Met Arg
            20

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gly His Pro Leu Leu Thr Lys Gln Leu Ala Cys Lys Arg Asp Ile Ala
1               5                   10                  15

<210> SEQ ID NO 195
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Gly Val Gln Thr Arg Asp Ser Val Lys Arg Ser Val Met
1               5                   10

```
<210> SEQ ID NO 196
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Gly Arg Ser His Ala Leu Asn Thr Ser Val Arg Gln Ile Thr Pro
1               5                   10                  15

Gln Tyr

<210> SEQ ID NO 197
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Asp Leu Leu Arg Lys Glu Ser Ser Gln Pro Arg Arg Leu Gln Asn Val
1               5                   10                  15

Ser Val

<210> SEQ ID NO 198
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Ala Thr Gly His Arg Asp Val Arg Pro Arg Met Val Asn
1               5                   10

<210> SEQ ID NO 199
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Arg Val Ser Asp Arg Ser Pro Val Arg Lys Met Ala Ile Gln His
1               5                   10                  15

<210> SEQ ID NO 200
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Val Ser Met Gly Lys Cys Phe Val Arg Asp Arg Thr Lys Val Glu
1               5                   10                  15

<210> SEQ ID NO 201
<211> LENGTH: 16
<212> TYPE: PRT
```

<210> SEQ ID NO 201
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Ser Gly Lys Leu Gly His Gln Trp Cys Thr Ile Ala Thr Pro Leu Lys
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 202

Ser Gly Ala Pro Met Val Cys Arg Thr Val Arg Leu Ser Thr Gln Gln
1               5                   10                  15

<210> SEQ ID NO 203
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

Glu Ser Arg Leu Asp Met Tyr Leu Ser Ala Phe Arg Lys Val Arg Asn
1               5                   10                  15

Thr Glu Ile Ile
            20

<210> SEQ ID NO 204
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 204

Gly Ser Gln Thr Gly Gln Ala Ser Arg Pro His Arg Asp Thr Thr Asn
1               5                   10                  15

<210> SEQ ID NO 205
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Thr Gly Ser Gln Pro Ile Val Met Arg Glu Arg Ala Thr Arg
1               5                   10

<210> SEQ ID NO 206
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

```
Leu Gly Asp Thr Asn Ser Thr Ile Arg Met Ser Ser Ser Ile Lys Pro
1               5                   10                  15

<210> SEQ ID NO 207
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Gly Lys Arg Met Lys Gln Leu Val Gln Leu Val Ala Thr
1               5                   10

<210> SEQ ID NO 208
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Ala Ala Gln Gln Ser Phe Arg Ile Thr Ser Pro Ser Val Ser Gln
1               5                   10                  15

Ile Pro

<210> SEQ ID NO 209
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Gly Arg Pro Ser Leu Lys Ala Gly Ala Lys Asp Ala Ile
1               5                   10

<210> SEQ ID NO 210
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Glu Ser Arg Ser Asp Met Asn Leu Ser Ala Phe Arg Lys Ala Arg Asn
1               5                   10                  15

Thr Glu Ile Ile
            20

<210> SEQ ID NO 211
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ser Gly Gly Arg Trp Phe Lys Gln Val Thr Arg Thr Ser Pro Ser Leu
1               5                   10                  15
```

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Asp Gly Arg Leu Lys Val Pro Trp Arg Thr Asp Tyr Pro Ser Lys Ala
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Thr Gly Lys Thr Ser Asp Trp Phe Thr Gly Asn Pro Arg Leu Leu Ser
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Gly Val Gln Arg Arg Cys Gly Tyr Trp Ala Pro Thr Val Ile Ser
1               5                   10                  15

<210> SEQ ID NO 215
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Leu Gly Tyr Pro Arg Glu Asp Val His Lys Lys Asn Met Lys His Arg
1               5                   10                  15

Pro Ile Val Ala
            20

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Gly Gly Ala Ala Ser Ala Ile Leu Val Asp Pro Val Leu Val Lys
1               5                   10                  15

<210> SEQ ID NO 217
<211> LENGTH: 16
<212> TYPE: PRT
<213> ORGANISM: Artificial Sequence
<220> FEATURE:

<223> OTHER INFORMATION: Description of Artificial Sequence: Synthetic
       peptide

<400> SEQUENCE: 217

Cys Ala Ala Gly Thr Arg Trp Asn Val Ala Ser Thr Arg Asp Tyr Glu
1               5                   10                  15

<210> SEQ ID NO 218
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 218

Gln Trp Gly Asn Thr Pro Trp Arg Pro Val Ala Arg Gln Val
1               5                   10

<210> SEQ ID NO 219
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 219

Ser Gly Arg Val Arg Met Asn Thr Arg Ser Ser Ser Ile Glu
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 220

Ser Gly Ser Ser Tyr Lys Gly Thr Arg Pro Arg Pro Val Lys
1               5                   10

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 221

Lys Glu Phe Trp Ala Arg Asn Tyr
1               5

<210> SEQ ID NO 222
<211> LENGTH: 22
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 222

Ser Gly Val Phe Arg Pro Gln Arg Arg Ser Ile Arg Pro Arg Asn Asn
1               5                   10                  15

Pro Gly Tyr Ser Leu Pro

20

<210> SEQ ID NO 223
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gln Ser Asn Val Thr Ala Pro Ser Thr His Arg Arg Pro Arg Lys Ile
1               5                   10                  15

Ser Asn Gly Val Ile Pro
            20

<210> SEQ ID NO 224
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Trp Gly Val Arg Thr Glu Ala Val Arg Ser Pro Leu Gln Ala Arg Asp
1               5                   10                  15

<210> SEQ ID NO 225
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ser Asp Ala Lys Pro Arg Asn Ala Ala Arg Ser Lys His Ala Leu Ser
1               5                   10                  15

Phe Val Gly Pro Arg Tyr
            20

<210> SEQ ID NO 226
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gln Ser Phe Pro Gly Thr Val Thr Asn Ala Arg Arg Leu Ala Asp Leu
1               5                   10                  15

Cys Thr Phe Pro Arg Ser
            20

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ala Thr Ser Leu Thr Pro Pro Phe Asp Val Asp Val Met Arg

```
1               5                   10

<210> SEQ ID NO 228
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Trp Gly Val Lys Ser His Asn Ala Arg His Gly Lys His Gly Gly Gln
1               5                   10                  15

<210> SEQ ID NO 229
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ser Glu Ala Lys Pro Arg Asn Ala Ala Arg Ser Lys His Ala Leu Ser
1               5                   10                  15

Phe Val Gly Pro Arg Tyr
            20

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Asp Val Arg Ser Thr Pro Pro Thr Asp Val Leu His Asp Val Tyr Ala
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ala Ser Glu Trp Leu Leu Asp Pro Lys Ile Tyr Gln His Ile Ala Ser
1               5                   10                  15

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ala Arg Asn Val Gly Met Asp Val Leu Gly Asp Val Tyr Met
1               5                   10

<210> SEQ ID NO 233
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 233

Thr Thr Leu Tyr Glu Val Tyr Arg
1               5

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Glu Trp Ser Met His Gln Glu Val Leu Asn
1               5                   10

<210> SEQ ID NO 235
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Ser Glu Asp Asp Val Phe Ser
1               5

<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Asp Pro Leu Glu Asp Val Phe Arg
1               5

<210> SEQ ID NO 237
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

His Met Met Ser Asp Val Tyr Lys
1               5

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gln Ser Gln Ser Asp Ile Tyr Ala
1               5
```

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Thr Pro Leu Trp Asp Thr Tyr Ala
1               5

<210> SEQ ID NO 240
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Thr Arg Ser Pro Phe Trp Asp Pro Arg Leu Leu
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Leu Ala Glu Asp Val Glu Arg Met Asp Val Leu Arg
1               5                   10

<210> SEQ ID NO 242
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Glu Val Arg Ser Thr Leu Pro Thr Asp Val Leu Gln Asp Val Tyr Thr
1               5                   10                  15

<210> SEQ ID NO 243
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Asp Lys Asn Pro Asp Asp Arg Ser Lys Lys Leu Asp Asp Val Phe Gln
1               5                   10                  15

<210> SEQ ID NO 244
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asp Ser Pro Tyr Ala Val Asn Asp Ser Asn Glu Asp Val Glu Asp Val
1               5                   10                  15

Tyr Arg

<210> SEQ ID NO 245
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asn Pro Gln Ser Ala Gly Ala Pro Ser Gly His Trp Leu Thr Thr Leu
1               5                   10                  15

Leu Glu

<210> SEQ ID NO 246
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ser Gly Arg Pro Ala Pro Val Leu Arg Gly Pro Ser Ser Arg Pro Ser
1               5                   10                  15

Arg Arg Lys Pro Lys Val
            20

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Thr Phe Gly Asp Leu Asp Asp Met Leu Arg
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gln Ala Thr Leu Trp Glu Glu Glu Leu Asp Glu Val Leu Arg
1               5                   10

<210> SEQ ID NO 249
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Asp Val Arg Ser Thr Pro Pro Met Asp Val Leu Gly Asp Val Tyr Met
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ala Ala Asn Asp Leu Pro Ser Arg Cys Asp Leu Gln Asp Ile Tyr Thr
1               5                   10                  15

<210> SEQ ID NO 251
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ser Glu Arg Arg Asn Thr Pro Ser Pro Met Arg Arg Glu Tyr Thr Arg
1               5                   10                  15

Asn Pro Ser Ala Leu Pro
            20

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Met Val Thr Ser Asp Pro Asp Ile Leu Ala
1               5                   10

<210> SEQ ID NO 253
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ser Cys Leu Glu Arg Ala Leu Pro Pro Arg Lys Arg Tyr Ser Arg Ser
1               5                   10                  15

Pro Ser Thr Cys
            20

<210> SEQ ID NO 254
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Met Gly Asp Glu His Arg Lys Leu Arg Leu Met Ser Gln Met Arg Leu
1               5                   10                  15

-continued

Gln Val Asp

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Lys Pro Arg Thr Asp Arg Lys Ile Phe Ser Leu Arg Leu Ala Asn
1               5                   10                  15

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Asn Pro Leu Pro Arg Asn Lys Tyr Pro Ser Pro Tyr Phe Leu His
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ala Pro Pro Ala Ala Ser Lys Ser Arg Thr Trp Glu Met Arg Arg
1               5                   10                  15

<210> SEQ ID NO 268
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Leu Asn Arg Pro Lys Leu Asn Thr Arg Pro His Tyr Thr Ser Val
1               5                   10                  15

<210> SEQ ID NO 269
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gln Thr Arg Pro Pro Arg Ser Phe Cys Met Leu Ala Met Thr Gly
1               5                   10                  15

<210> SEQ ID NO 270
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Met His Gly Pro Arg Leu Pro Pro Leu Lys Leu Cys Gly Ala Trp Ser
1               5                   10                  15

Ile Gly

<210> SEQ ID NO 271
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gly Pro Arg Val Val Thr Arg Arg Val Leu Ala Thr Val Thr Val Ala
1               5                   10                  15

<210> SEQ ID NO 272
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Leu Gly Met Val Ser Arg Pro Arg Leu Asn Gln Arg Ala Pro Ile Pro
1               5                   10                  15

Lys Ser

<210> SEQ ID NO 273
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gln Tyr Pro Arg His Pro Thr Thr Ser Lys Arg Ile Gly Pro Thr Asp
1               5                   10                  15

Arg Val Leu Thr
            20

<210> SEQ ID NO 274
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Tyr Pro Arg Glu Ala Thr Ser Arg Arg Glu Thr Asp Ile Leu Asn Ser
1               5                   10                  15

Lys Arg Leu Leu Ser
            20

<210> SEQ ID NO 275
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Gln Cys Asn Pro Val Leu Lys Cys Arg Thr Ile Lys Pro Gly Pro Ser
1               5                   10                  15

Ala Ala

<210> SEQ ID NO 276
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Gln Pro Thr Trp Met Lys Ser Pro Arg Lys Lys Arg Tyr Pro Thr Gly
1               5                   10                  15

Arg Leu Thr Ala Gln
            20

<210> SEQ ID NO 277
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Asp Pro Glu Tyr Leu Ser Gln Arg Val Pro Arg Arg Arg Gln Lys Pro
1               5                   10                  15

Pro Met Thr Arg Pro Tyr
            20

<210> SEQ ID NO 278
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Met Glu Gln Arg Val Arg Ala Thr Asn Pro Arg Arg Arg Leu Ala Ile
1               5                   10                  15

Leu Thr Thr Glu Ser Phe Met
            20

<210> SEQ ID NO 279
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gln Ser Pro Asn Met Ile Gln Arg Thr Pro Lys Arg Arg Thr Pro Leu
1               5                   10                  15

Thr Ile Pro Leu Arg
            20

<210> SEQ ID NO 280
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 280

Ala Gly Asn Cys Ala Arg Leu Thr Val Arg Pro Pro Phe Ser His Pro
1               5                   10                  15

<210> SEQ ID NO 281
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Glu Arg Pro Pro Arg Ser Leu Ala Ser Pro His Ala Leu Leu Leu
1               5                   10                  15

<210> SEQ ID NO 282
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Ile His Gly Val Pro Ala Ala Met Ala Glu Arg Pro Phe Gln Cys
        35                  40                  45

Arg Ile Cys Met Arg Asn Phe Ser Asp Arg Ser Asn Leu Ser Arg His
    50                  55                  60

Ile Arg Thr His Thr Gly Glu Lys Pro Phe Ala Cys Asp Ile Cys Gly
65                  70                  75                  80

Arg Lys Phe Ala Ile Ser Ser Asn Leu Asn Ser His Thr Lys Ile His
                85                  90                  95

Thr Gly Ser Gln Lys Pro Phe Gln Cys Arg Ile Cys Met Arg Asn Phe
            100                 105                 110

Ser Arg Ser Asp Asn Leu Ala Arg His Ile Arg Thr His Thr Gly Glu
        115                 120                 125

Lys Pro Phe Ala Cys Asp Ile Cys Gly Arg Lys Phe Ala Thr Ser Gly
    130                 135                 140

Asn Leu Thr Arg His Thr Lys Ile His Leu Arg Gly Ser Gln Leu Val
145                 150                 155                 160

Lys Ser Glu Leu Glu Glu Lys Lys Ser Glu Leu Arg His Lys Leu Lys
                165                 170                 175

Tyr Val Pro His Glu Tyr Ile Glu Leu Ile Glu Ile Ala Arg Asn Ser
            180                 185                 190

Thr Gln Asp Arg Ile Leu Glu Met Lys Val Met Glu Phe Phe Met Lys
        195                 200                 205

Val Tyr Gly Tyr Arg Gly Lys His Leu Gly Gly Ser Arg Lys Pro Asp
    210                 215                 220

Gly Ala Ile Tyr Thr Val Gly Ser Pro Ile Asp Tyr Gly Val Ile Val
225                 230                 235                 240

Asp Thr Lys Ala Tyr Ser Gly Gly Tyr Asn Leu Pro Ile Gly Gln Ala
                245                 250                 255

Asp Glu Met Gln Arg Tyr Val Glu Glu Asn Gln Thr Arg Asn Lys His

-continued

```
                260                 265                 270
Ile Asn Pro Asn Glu Trp Trp Lys Val Tyr Pro Ser Ser Val Thr Glu
            275                 280                 285

Phe Lys Phe Leu Phe Val Ser Gly His Phe Lys Gly Asn Tyr Lys Ala
        290                 295                 300

Gln Leu Thr Arg Leu Asn His Ile Thr Asn Cys Asn Gly Ala Val Leu
305                 310                 315                 320

Ser Val Glu Glu Leu Leu Ile Gly Gly Glu Met Ile Lys Ala Gly Thr
                325                 330                 335

Leu Thr Leu Glu Glu Val Arg Arg Lys Phe Asn Asn Gly Glu Ile Asn
            340                 345                 350

Phe
```

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

```
Leu Arg Gly Ser Gln Leu Val Lys Ser
1               5
```

<210> SEQ ID NO 284
<211> LENGTH: 9
<212> TYPE: PRT
<213> ORGANISM: Unknown
<220> FEATURE:
<223> OTHER INFORMATION: Description of Unknown:
      "LAGLIDADG" family motif peptide

<400> SEQUENCE: 284

```
Leu Ala Gly Leu Ile Asp Ala Asp Gly
1               5
```

<210> SEQ ID NO 285
<211> LENGTH: 25
<212> TYPE: DNA
<213> ORGANISM: Homo sapiens

<400> SEQUENCE: 285
ctgacctctt ctcttcctcc cacag                                    25

<210> SEQ ID NO 286
<211> LENGTH: 13
<212> TYPE: DNA
<213> ORGANISM: Homo sapiens

<400> SEQUENCE: 286
tttctctcca cag                                                 13

COMPOSITIONS FOR LINKING DNA-BINDING DOMAINS AND CLEAVAGE DOMAINS

CROSS-REFERENCE TO RELATED APPLICATIONS

The present application is a divisional of U.S. application Ser. No. 15/380,784, filed Dec. 15, 2016, which claims the benefit of U.S. Provisional Application No. 62/290,065, filed Feb. 2, 2016, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 18, 2020, is named 8325014810SL.txt and is 76,723 bytes in size.

STATEMENT OF RIGHTS TO INVENTIONS MADE UNDER FEDERALLY SPONSORED RESEARCH

Not applicable.

Technical Field

The present disclosure is in the fields of genome and protein engineering.

Background

Artificial nucleases, such as engineered zinc finger nucleases (ZFN), transcription-activator like effector nucleases (TALENs), the CRISPR/Cas system with an engineered crRNA/tracr RNA ('single guide RNA') and/or nucleases based on the Argonaute system (e.g., from *T. thermophilus*, known as 'TtAgo', (Swarts et al. (2014) *Nature* 507(7491): 258-261), comprising DNA binding domains (nucleotide or polypeptide) operably linked to cleavage domains have been used for targeted alteration of genomic sequences. For example, nucleases have been used to insert exogenous sequences, inactivate one or more endogenous genes, create organisms (e.g., crops) and cell lines with altered gene expression patterns, and the like. See, e.g., U.S. Pat. Nos. 9,255,250; 9,045,763; 9,005,973; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; and 8,409,861; U.S. Patent Publication Nos. 2003/0232410; 2005/0208489; 2005/0026157; 2005/0064474; 2006/0063231; 2008/0159996; 2010/00218264; 2012/0017290; 2011/0265198; 2013/0137104; 2013/0122591; 2013/0177983; 2013/0177960; and 2015/0056705. For instance, a pair of nucleases (e.g., zinc finger nucleases, TALENs) may be used to cleave genomic sequences. Each member of the pair generally includes an engineered (non-naturally occurring) DNA-binding protein linked to one or more cleavage domains (or half-domains) of a nuclease. When the DNA-binding proteins bind to their target sites, the cleavage domains that are linked to those DNA binding proteins are positioned such that dimerization and subsequent cleavage of the genome can occur, generally between the pair of the zinc finger nucleases or TALENs.

It has been shown that cleavage activity of the nuclease pair is related to the length of the linker joining the zinc finger and the cleavage domain ("ZC" linker), the amino acid composition, and the distance (gap) between the target sites (binding sites). See, for example, U.S. Pat. Nos. 9,394,531; 8,772,453; 7,888,121 and 8,409,861; Smith et al. (2000) *Nucleic Acids Res.* 28:3361-3369; Bibikova et al. (2001) *Mol. Cell. Biol.* 21:289-297; U.S. Patent Publication No. 2015/0064789. When using pairs of nuclease fusion proteins, optimal cleavage with currently available ZC linkers and cleavage half domains has been obtained when the binding sites for the fusion proteins are located 5 or 6 nucleotides apart (as measured from the near edge of each binding site). See, e.g., U.S. Pat. No. 7,888,121. U.S. Patent Publication Nos. 2009/0305419 and 2015/0064789 describe linking DNA-binding domains and cleavage domains by using various linker sequences (for various gap spacings) and/or modifying the N-terminal residues of the FokI cleavage domain.

However, there remains a need for methods and compositions that allow targeted modification where the artificial nucleases can cleave endogenous genomic sequences in alternative architectures and with binding site separations of 6, 7, 8 or more base pairs.

SUMMARY

Disclosed herein are compositions for linking DNA-binding domains and cleavage domains to form nucleases, for example nucleases with the same or altered target site configurations (architectures) and/or separation (gap) preferences as compared to conventional linkers (which use a tail-to-tail architecture), including, but not limited to, head-to-tail architectures (in which the DNA-binding domains of a dimer bind to the same strand of DNA), head-to-head architectures (in which the DNA-binding domains are operably linked to the N-terminal of the cleavage domain) and symmetric and asymmetric tail-to-tail architectures. Also described are fusion molecules comprising these linkers as well as dimers of these fusion molecules for use in targeted cleavage of DNA. The disclosure also provides methods of using these fusion molecules and compositions thereof for targeted cleavage of cellular chromatin in a region of interest and/or homologous recombination at a predetermined region of interest in cells.

Thus, in one aspect, described herein are amino acid sequences for use in linking a DNA-binding domain (e.g., zinc finger protein, TAL-effector domain or single guide (sg) RNA of a CRISPR/Cas nuclease system) to a functional domain such as a nuclease (cleavage) domain (e.g., wild type or engineered FokI cleavage domain). A linker is used to link any DNA-binding domain to the functional domain (e.g., cleavage domain). In certain embodiments, the linker extends from the N- or C-terminal of a protein DNA binding domain (ZFP or TALE) or from the 5' or 3' end of a polynucleotide DNA-binding domain (e.g., sgRNA). In certain embodiments, the amino acid linker sequences extend between the last residue of the either N- or C-terminal of a protein DNA-binding domain and the N- or C-terminal of the cleavage domain. In other embodiments, the amino acid linkers sequences associates with any portion of a polynucleotide DNA-binding domain (e.g., sgRNAs). The linker can be of any length, for example, between 4 and 22 amino acids in length including 8, 9, 10, 11, 12, 13, 14, 15, 16, 17 or more residues in length. In other embodiments, the linker comprises any of the linkers shown in FIG. 4, 5, 6, 7, 8, 9, 11 or 19 (SEQ ID NO:6-281). In certain embodiments, the linker comprises a linker as shown in FIG. 11 or FIG. 19B. Furthermore, the linkers may be used for paired target sites separated by 5, 6, 7, 8, 9, 10, 11 or more base pairs.

In still further aspects, described herein is a fusion molecule comprising a DNA-binding domain (e.g., zinc finger protein, TALE, sgRNA), a function domain (e.g., a nuclease cleavage domain (e.g., FokI, Cas nuclease, etc.) and also comprises a linker as described herein between (linking) the DNA-binding domain and the functional domain. In certain embodiments, the fusion molecule comprises a DNA-binding domain, a cleavage domain and a linker between the DNA-binding domain and the cleavage domain, wherein the linker comprises or consists of a sequence as shown in any of SEQ ID NO:6-281. In certain embodiments, the linker comprises or consists of the linkers as shown in FIG. 11 or FIG. 19B. In certain embodiments, the fusion molecule comprises a DNA-binding domain (e.g., ZFP or TALE) and a FokI cleavage domain at the N- or C-terminal of the DNA-binding domain. In certain embodiments, the linker extends between the N-terminal of the DNA-binding domain and C-terminal of the cleavage domain. The nuclease cleavage domain may be modified in any way, including addition, deletion and/or substitution of one or more amino acids residues. Any of the fusion molecules may comprise wild-type or engineered cleavage domains, including but not limited cleavage domains with one or more modifications to the dimerization interface such that only heterodimers are formed and/or one or more modifications to the catalytic domain such that the nuclease is a nickase in that it makes a single-stranded cut. In certain embodiments, the cleavage domain can be cleavage half-domain.

In another aspect, described herein is a dimer comprising a first fusion molecule comprising a linker as described herein, and a second fusion molecule comprising a second DNA-binding domain and a second wild-type or engineered cleavage domain. In certain embodiments, at least one fusion molecule comprises a linker as described herein. In other embodiments, both fusion molecules comprise a linker as described herein. In still further embodiments, the DNA-binding domains of the dimer target sequences (e.g., in double-stranded DNA) separated by 5, 6, 7, 8, 9, 10, 11, 12, 13, 14, 15, 16 (or more) base pairs, preferably 6 to 11 base pairs. Importantly, the linkers described herein allow the dimers to form when the components are bound to opposite DNA strands in conventional tail-to-tail configuration (using either symmetric or asymmetric linkers) and/or when the components are bound to the same DNA strand (head-to-tail) or opposite DNA strands in alternative (e.g., head-to-head) configurations. Thus, the linkers described herein provide for dimers (with any DNA-binding domain) in which the endonuclease (e.g., FokI) cleavage domains are in novel head-to-head or head-to-tail configurations or tail-to-tail configurations. See, e.g., FIG. 1B, 1C and FIG. 19B. These configurations may be employed using any DNA-binding domain, including but not limited to zinc finger protein DNA binding domains, TAL-effector DNA binding domains and sgRNAs. Thus, any of the dimers described herein, may bind to opposite or the same strand of DNA in a double-stranded target DNA and may make a double- or single-stranded cut in a target double-stranded DNA.

In another aspect, polynucleotides encoding any of the linkers or fusion molecules (or components thereof) as described herein are provided. In some embodiments, the polynucleotides are RNAs.

In yet another aspect, cells comprising any of the polypeptides (e.g., fusion molecules) and/or polynucleotides as described herein are also provided. In one embodiment, the cells comprise a pair of fusion molecules, each comprising a linker (and/or cleavage domain) as disclosed herein.

In yet another aspect, methods for targeted cleavage of cellular chromatin in a region of interest of a genome; methods of causing homologous recombination to occur in a cell; methods of treating infection; and/or methods of treating disease are provided. The methods involve cleaving cellular chromatin at a predetermined region of interest in cells by expressing a pair of fusion molecules, at least one of which comprises a linker as described herein. In certain embodiments, one fusion polypeptide comprises a linker as described herein and in other embodiments, both fusion molecules comprise a linker as described herein. Furthermore, in any of the methods described herein, the pair of fusion polypeptides cleaves the targeted region when the binding sites for the zinc finger nucleases are 5, 6, 7, 8, 9, 10, 11 or even more base pairs apart. In certain embodiments, each member of the pair binds to the same strand of DNA. In other embodiments, each member of the pair binds to opposite DNA strands in a head-to-head or tail-to-tail configuration. Targeted cleavage can result in modification of the target DNA, including via insertions and/or deletions (via non-homologous and/or homologous repair mechanisms), including integration of a donor (e.g., transgene) sequence.

The linkers as described herein can be used in methods for targeted cleavage of cellular chromatin in a region of interest and/or homologous recombination at a predetermined region of interest in cells. Cells include cultured cells, cells in an organism and cells that have been removed from an organism for treatment in cases where the cells and/or their descendants will be returned to the organism after treatment. A region of interest in cellular chromatin can be, for example, a genomic sequence or portion thereof.

A fusion molecule can be expressed in a cell, e.g., by delivering the fusion molecule (or components thereof) to the cell or by delivering a polynucleotide encoding the fusion molecule to a cell, wherein the polynucleotide, if DNA, is transcribed, and an RNA molecule delivered to the cell or a transcript of a DNA molecule delivered to the cell is translated, to generate the fusion protein. Methods for polynucleotide and polypeptide delivery to cells are presented elsewhere in this disclosure.

Accordingly, in another aspect, a method for cleaving cellular chromatin in a region of interest can comprise (a) selecting a first sequence in the region of interest; (b) engineering a first DNA-binding domain to bind to the first sequence; (c) expressing a first fusion molecule in the cell, the first fusion molecule comprising the first DNA-binding domain (e.g., zinc finger, TALE, sgRNA), and a cleavage domain (or half-domain); and (d) expressing a second fusion protein in the cell, the second fusion molecule comprising a second DNA-binding domain, and a second cleavage domain (or half-domain), wherein at least one of the fusion molecules comprises a linker as described herein, and further wherein the first fusion molecule binds to the first sequence, and the second fusion molecule binds to a second sequence located between 2 and 50 nucleotides from the first sequence, such that cellular chromatin is cleaved in the region of interest. In certain embodiments, both fusion molecules comprise a linker as described herein.

In other embodiments, the disclosure provides methods of cleaving cellular chromatin by introducing one more nucleases comprising a linker as described herein into a cell such that the nucleases target and cleave the cellular chromatin of the cell. The nuclease may comprise a zinc finger nuclease (ZFN), a TALE-nuclease (TALEN), TtAgo or a CRISPR/

Cas nuclease system or a combination thereof. The nuclease(s) may be introduced into the cell in any form, for example in protein form, in mRNA form or carried on a viral (AAV, IDLV, etc.) vector or non-viral vector (e.g., plasmid). In certain embodiments, the methods comprise (a) selecting first and second sequences in a region of interest, wherein the first and second sequences are between 2 and 50 nucleotides apart; (b) engineering a first DNA-binding domain to bind to the first sequence; (c) engineering a second DNA-binding domain to bind to the second sequence; (d) expressing a first fusion molecule in the cell, the first fusion molecule comprising the first engineered DNA-binding domain, a first linker as described herein, and a first cleavage domain (or half domain); (e) expressing a second fusion molecule in the cell, the second fusion molecule comprising the second engineered DNA-binding domain, a second linker and a second cleavage half-domain; wherein the first fusion molecule binds to the first sequence and the second fusion molecule binds to the second sequence, thereby cleaving the cellular chromatin in the region of interest. In certain embodiments, the first and second fusion molecule comprise a linker as described herein.

Also provided are methods of altering a region of cellular chromatin, for example to introduce targeted mutations. In certain embodiments, methods of altering cellular chromatin comprise introducing into the cell one or more targeted nucleases to create a double-stranded break in cellular chromatin at a predetermined site, and a donor polynucleotide, having homology to the nucleotide sequence of the cellular chromatin in the region of the break. Cellular DNA repair processes are activated by the presence of the double-stranded break and the donor polynucleotide is used as a template for repair of the break, resulting in the introduction of all or part of the nucleotide sequence of the donor into the cellular chromatin. Thus, a sequence in cellular chromatin can be altered and, in certain embodiments, can be converted into a sequence present in a donor polynucleotide.

Targeted alterations include, but are not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations.

The donor polynucleotide can be DNA or RNA, can be linear or circular, and can be single-stranded or double-stranded. It can be delivered to the cell as naked nucleic acid, as a complex with one or more delivery agents (e.g., liposomes, poloxamers) or contained in a viral delivery vehicle, such as, for example, an adenovirus or an adeno-associated virus (AAV). Donor sequences can range in length from 10 to 1,000 nucleotides (or any integral value of nucleotides therebetween) or longer. In some embodiments, the donor comprises a full-length gene flanked by regions of homology with the targeted cleavage site. In some embodiments, the donor lacks homologous regions and is integrated into a target locus through homology independent mechanism (i.e. NHEJ). In other embodiments, the donor comprises a smaller piece of nucleic acid flanked by homologous regions for use in the cell (i.e. for gene correction). In some embodiments, the donor comprises a gene encoding a functional or structural component such as a shRNA, RNAi, miRNA or the like. In other embodiments, the donor comprises sequences encoding a regulatory element that binds to and/or modulates expression of a gene of interest. In other embodiments, the donor is a regulatory protein of interest (e.g., ZFP TFs, TALE TFs or a CRISPR/Cas TF) that binds to and/or modulates expression of a gene of interest.

In certain embodiments, the frequency of homologous recombination can be enhanced by arresting the cells in the G2 phase of the cell cycle and/or by activating the expression of one or more molecules (protein, RNA) involved in homologous recombination and/or by inhibiting the expression or activity of proteins involved in non-homologous end-joining.

In any of the methods described herein in which a pair of nucleases is used, the first and second nucleases of the nuclease pair can bind to target sites 2, 3, 4, 5, 6, 7, 8, 9, 10, 11, 12, 13, 14, 15, 16, 17, 18, 19, 20 or more base pairs apart. In certain embodiments, the target sites of a paired target site are 6, 7, 8, 9 or 10 base pairs apart. In addition, in any of the methods, the second zinc finger binding domain may be engineered to bind to the second sequence.

Furthermore, in any of the methods described herein, the fusion molecules may be encoded by a single polynucleotide.

For any of the aforementioned methods, the cellular chromatin can be in a chromosome, episome or organellar genome. Cellular chromatin can be present in any type of cell including, but not limited to, prokaryotic and eukaryotic cells, fungal cells, plant cells, animal cells, mammalian cells, primate cells and human cells.

In another aspect, described herein is a kit comprising a linker as described herein or a polynucleotide encoding a linker as described herein; ancillary reagents; and optionally instructions and suitable containers. The kit may also include one or more nucleases or polynucleotides encoding such nucleases.

In any of the proteins, methods and kits described herein, the cleavage domain (or cleavage half-domain) may comprise a TypeIIS cleavage domain, such as a cleavage half-domain from FokI.

These and other aspects will be readily apparent to the skilled artisan in light of disclosure as a whole.

BRIEF DESCRIPTION OF THE DRAWINGS

FIG. 1A shows the typical architecture currently used. FIG. 1B shows a head-to-tail architecture. FIG. 1C shows a head-to-head architecture.

FIGS. 3A through 3F depict ccdB induction using the screening procedure described in U.S. Patent Publication No. 2015/0064789. Briefly, bacterial cells harboring a ccdB plasmid with a target site separated by the indicated spacing and the constant partner ZFN were transformed with the second ZFN containing a linker library between the N-terminal FokI domain and the C-terminal ZFP binding domain. ZFN expression was induced followed by induction of the ccdB toxin. Cells were incubated overnight and a sample was plated on LB, ampicillin/spectinomycin (A/S), and kanamycin (Kan) plates. Selected linkers were subcloned into a fresh vector and the selection was repeated for nine rounds. The left bar of each graph shows the cell number on LB plates. The middle bar shows the cell number on A/S plates and the left bar shows cell number on Kan plates. FIG. 3A shows ccdB induction results using 6 base pair spacing between target sites; FIG. 3B shows ccdB induction results using 7 base pair spacing between target sites; FIG. 3C shows ccdB induction results using 8 base pair spacing between target sites; FIG. 3D shows ccdB induction results using 9 base pair spacing between target sites; FIG. 3E shows ccdB induction results using 10 base pair spacing between target sites; and FIG. 3F shows ccdB induction results using 11 base pair spacing between target sites;

FIG. 4 (SEQ ID NOs:6-84) shows exemplary linkers obtained from bacterial selections after the indicated round using libraries of linkers of 4 to 22 amino acids.

FIG. 5 (SEQ ID NOs:85-161) shows exemplary linkers obtained from bacterial selections using libraries of linkers of 4 to 22 amino acids for the target spacings of 7 base pairs.

FIG. 6 (SEQ ID NOs:162-220) shows exemplary linkers obtained from bacterial selections using libraries of linkers of 4 to 22 amino acids for the target spacings of 8 base pairs.

FIG. 7 (SEQ ID NOs:221-229) shows exemplary linkers obtained from bacterial selections using libraries of linkers of 4 to 22 amino acids for the target spacings of 9 base pairs.

FIG. 8 (SEQ ID NOs:230-253) shows exemplary linkers obtained from bacterial selections using libraries of linkers of 4 to 22 amino acids for the target spacings of 10 base pairs.

FIGS. 10A through 10D show nuclease activity (NHEJ activity) with the indicated linkers on the indicated target sites. As in FIG. 9, the CCR5 ZFNs were tested in cell lines with the CCR5 target site with the indicated spacing at the AAVS1 locus and vice versa. FIG. 10A shows nuclease activity using linkers selected from the 6 bp spacing screen where the DNA-binding domain is targeted to CCR5. FIG. 10B shows nuclease activity using linkers selected from the 6 bp spacing screen where the DNA-binding domain is targeted to AAVS1. FIG. 10C shows nuclease activity using linkers selected from the 7 bp spacing screen where the DNA-binding domain is targeted to CCR5. FIG. 10B shows nuclease activity using linkers selected from the 7 bp spacing screen where the DNA-binding domain is targeted to AAVS1. In FIGS. 10A and 10C, the left most bar shows activity at 6 bp spacing; the bar second from the left shows activity at 7 bp spacing; the bar third from the left shows activity at 8 bp spacing; the middle bar shows activity at 9 bp spacing; the bar third from the right shows activity at 10 bp spacing; the bar second from the right shows activity at 11 bp spacing; and the right most bar shows activity on the wild-type CCR5 target site at the AAVS1 locus (AW). In FIGS. 10B and 10D, the left most bar shows activity at 6 bp spacing; the bar second from the left shows activity at 7 bp spacing; the bar third from the left shows activity at 8 bp spacing; the bar third from the right shows activity at 9 bp spacing; the bar second from the right shows activity at 10 bp spacing; and the right most bar shows activity on the wild-type AAVS1 target site at the CCR5 locus (CW).

FIG. 11 (SEQ ID NOs:78, 62, 80, 81, 71, 82, 83 and 84 (L1 to L8 for 6 bp spacing) and 88, 109, 114, 100, 91, 138, 147, 154 (L1 to L8 for 7 bp spacing)) shows the linkers selected for further testing in portability studies.

FIG. 12 shows the experimental setup for the portability studies. Ten ZFN pairs were designed for each of the following architectures: 1) tail-to-tail architecture, 2) head-to-tail architecture with a 6 base pair spacing, 3) head-to-tail architecture with a 7 base pair spacing, and 4) head-to-tail architecture with an 8 base pair spacing. For both the 7 and 8 base pair spacings between the target sites of the DNA-binding domains of the dimer, an additional linker (L7c5) was also tested for comparison to the standard linker (L0) in the constant ZFN (ZFN #1). 6.1-6.8 for ZFN #2 represents linkers L1-L8 selected for a 6 base pair spacing (see FIG. 10). 7.1-7.8 for ZFN #2 represents linkers L1-L8 selected for a 7 base pair spacing (see FIG. 10). 8.1-8.2 for ZFN #2 represents linkers selected for an 8 base pair spacing (not shown).

FIG. 13 shows results (NHEJ percentage) of portability studies conducted with various linkers in the head-to-tail architecture with a 6 base pair spacing between the target sites. L0 pairs indicate those pairs using the tail-to-tail architecture.

FIG. 14 shows results (NHEJ percentage) of portability studies conducted with various linkers in the head-to-tail architecture with a 7 bp spacing between the target sites of the nuclease dimer. L0 pairs indicate those pairs using the tail-to-tail architecture.

FIG. 15 is a comparison of the obligate heterodimer FokI domain polarity on the NHEJ activity for the indicated ZFNs from the portability study (see FIGS. 11 and 13; L7/N6a (SEQ ID NO:83); L5/N6b (SEQ ID NO:71); L8/N6c (SEQ ID NO:84); L8/N7a (SEQ ID NO:154); L3/N7b (SEQ ID NO:114); L4/N7c (SEQ ID NO:100)). ZFNs were tested with the FokI domains in either possible orientation.

FIG. 16 is a summary of NHEJ activity of AAVS1-targeted nucleases with the indicated linkers in the tail-to-tail configuration (left panel); head-to-tail 6 bp spacing configuration (middle panel) and head-to-tail 7 bp spacing configuration (right panel). The ZFNs were targeted to a hypersensitive site within intron 1 of the AAVS1 gene.

FIG. 18 is a summary of NHEJ activity of AAVS1-targeted nucleases with the indicated linkers (N6a, SEQ ID NO:83: N6b, SEQ ID NO:71; N7a, SEQ ID NO:154 and N7b, SEQ ID NO:114), at the indicated spacing in a head-to-head configuration.

FIGS. 19A and 19B show results from the selection of linkers in a tail-to-tail architecture using either symmetric or asymmetric linkers. FIG. 19A shows the experimental setup for the selection and the selection procedure is described in U.S. Patent Publication No. 2015/0064789. FIG. 19B shows exemplary linkers (SEQ ID Nos: 254, 255, 266-281) selected at the indicated spacing and the in vivo activity of these linkers in the CCR5 ZFNs at the CCR5 locus with the indicated configuration and spacing. Also shown are AAVS1 controls for each cell line.

DETAILED DESCRIPTION

Described herein are compositions for linking DNA-binding domains and cleavage domains to form artificial nucleases and methods of using these nucleases for targeted alteration of a cellular nucleotide sequence, e.g., by targeted cleavage followed by non-homologous end joining; by targeted cleavage followed by homologous recombination between an exogenous polynucleotide (comprising one or more regions of homology with the cellular nucleotide sequence) and a genomic sequence; by targeted inactivation of one or more endogenous genes.

Figure 1A:
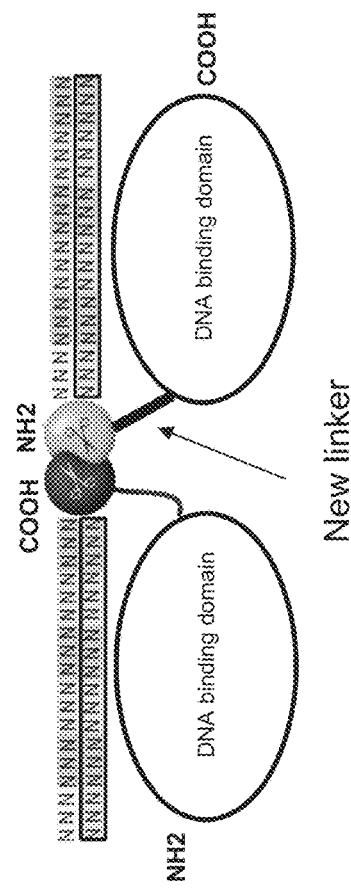
FIGS. 1A through 1C depict exemplary architectures of nuclease designs.
Figure 1B:
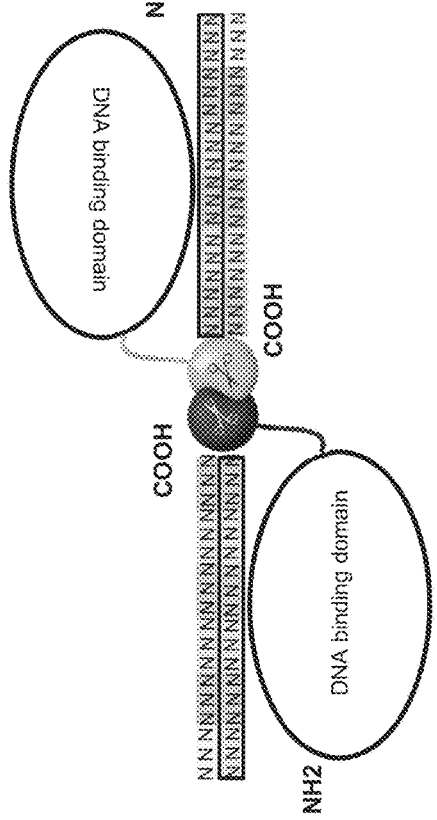
Figure 1C:
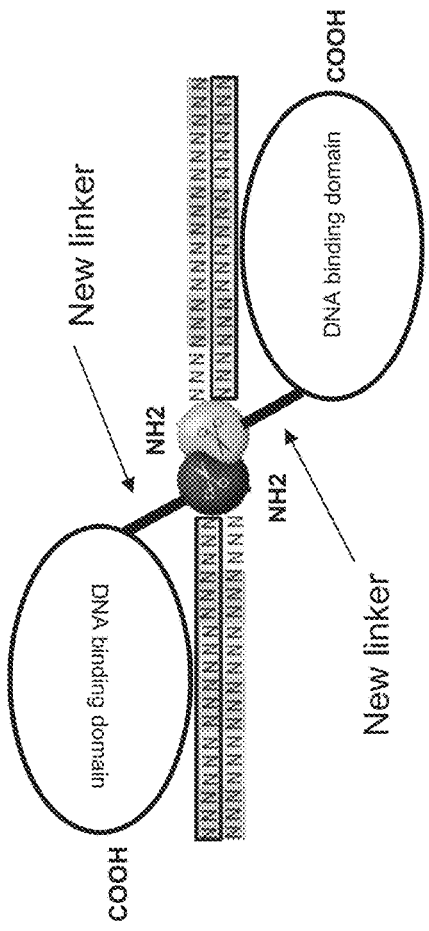

The invention includes protein (amino acid) linkers placed between a cleavage domain (or half-domain) and a DNA binding domain such that the nuclease is active in configurations other than the conventional configuration (FIG. 1A). The linker may be positioned so that it extends between the N- or C-terminal of the DNA-binding domain and the N- or C-terminal of the nuclease (cleavage) domain. Thus, the linkers as described herein provide nuclease dimers that are active when in a head-to-tail architecture (where both DNA-binding components of the dimer bind to the same DNA strand, FIG. 1B) and in head-to-head configurations (FIG. 1C). Any DNA-binding domain can be used with these linkers to provide the desired configuration, for example, zinc finger proteins, TAL-effector domain binding proteins, sgRNAs, etc.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}M^{-1}$ or lower. "Affinity" refers to the strength of binding: increased binding affinity being correlated with a lower $K_d$. "Non-specific binding" refers to, non-covalent interactions that occur between any molecule of interest (e.g., an engineered nuclease) and a macromolecule (e.g., DNA) that are not dependent on target sequence.

A "DNA binding molecule" is a molecule that can bind to DNA. Such DNA binding molecule can be a polypeptide, a domain of a protein, a domain within a larger protein or a polynucleotide. In some embodiments, the polynucleotide is DNA, while in other embodiments, the polynucleotide is RNA. In some embodiments, the DNA binding molecule is a protein domain of a nuclease (e.g., the FokI domain), while in other embodiments, the DNA binding molecule is a guide RNA component of an RNA-guided nuclease (e.g., Cas9 or Cfp1).

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. Nos. 8,586,526 and 9,458,205.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs (canonical and non-canonical RVDs) and binding data. See, for example, U.S. Pat. Nos. 9,458,205; 8,586,526; 6,140,081; 6,453,242; and 6,534,261; see also International Patent Publication Nos. WO 98/53058; WO 98/53059; WO 98/53060; WO 02/016536; and WO 03/016496.

A "selected" zinc finger protein, TALE protein or CRISPR/Cas system is not found in nature and whose production results primarily from an empirical process such as phage display, interaction trap or hybrid selection. See e.g., U.S. Pat. Nos. 5,789,538; 5,925,523; 6,007,988; 6,013,453; and 6,200,759; International Patent Publication Nos. WO 95/19431; WO 96/06166; WO 98/53057; WO 98/54311; WO 00/27878; WO 01/60970; WO 01/88197; and WO 02/099084 and U.S. Patent Publication No. 2011/0301073.

"TtAgo" is a prokaryotic Argonaute protein thought to be involved in gene silencing. TtAgo is derived from the bacteria *Thermus thermophilus*. See, e.g., Swarts et al., ibid, G. Sheng et al. (2013) *Proc. Natl. Acad. Sci. U.S.A.* 111: 652). A "TtAgo system" is all the components required including, for example, guide DNAs for cleavage by a TtAgo enzyme.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and – cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 8,623,618; 7,888,121; 7,914,796; and 8,034,598 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. With respect to sequences described herein, the range of desired degrees of sequence identity is approximately 80% to 100% and any integer value therebetween. Typically, the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, DC; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, DC; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. "Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule, a malfunctioning version of a normally-functioning endogenous molecule or an ortholog (functioning version of endogenous molecule from a different species).

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. See, e.g., U.S. Pat. Nos. 8,703,489 and 9,255,250. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of fusion molecules include, but are not limited to, fusion proteins (for example, a fusion between a protein DNA-binding domain and a cleavage domain), fusions between a polynucleotide DNA-binding domain (e.g., sgRNA) operatively associated with one or more cleavage domains, and fusion nucleic acids (for example, a nucleic acid encoding the fusion protein).

Expression of a fusion molecule in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" or "modification" of gene expression refers to a change in the activity of a gene. Modulation of expression can include, but is not limited to, gene activation and gene repression, including by modification of the gene via binding of an exogenous molecule (e.g., engineered transcription factor). Modulation may also be achieved by modification of the gene sequence via genome editing (e.g., cleavage, alteration, inactivation, random mutation). Gene inactivation refers to any reduction in gene expression as compared to a cell that has not been modified as described herein. Thus, gene inactivation may be partial or complete.

"Eukaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain is fused to a cleavage domain, the DNA-binding domain and the cleavage domain are in operative linkage if, in the fusion polypeptide, the DNA-binding domain portion is able to bind its target site and/or its binding site, while the cleavage domain is able to cleave DNA in the vicinity of the target site (e.g., 1 to 500 base pairs or any value therebetween on either side of the target site).

In the methods of the disclosure, one or more targeted nucleases as described herein create a double-stranded break (DSB) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

Additional pairs of zinc-finger proteins, TALENs, TtAgo or CRIPSR/Cas systems can be used for additional double-stranded cleavage of additional target sites within the cell.

In any of the methods described herein, additional pairs of zinc-finger proteins, TALENs, TtAgo or CRIPSR/Cas systems can be used for additional double-stranded cleavage of additional target sites within the cell.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and International Patent Publication No. WO 98/44350.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the expression cassettes of the invention can be administered. Subjects of the present invention include those with a disorder or those at risk for developing a disorder.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Cancer and graft versus host disease are non-limiting examples of conditions that may be treated using the compositions and methods described herein. Thus, "treating" and "treatment" includes:

(i) preventing the disease or condition from occurring in a mammal, in particular, when such mammal is predisposed to the condition but has not yet been diagnosed as having it;

(ii) inhibiting the disease or condition, i.e., arresting its development; q(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment in the mammal, preferably a human. The amount of a composition of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

Linkers

Described herein are amino acid sequences that fuse (link) a DNA binding domain (e.g., zinc finger protein, TALE, sgRNA, etc.) and a nuclease (e.g., a cleavage domain or cleavage half-domain).

Currently, nuclease dimers bind to opposite DNA strands (see, FIG. 1A), which can limit the design of nucleases. The linkers described herein allow for binding in both the current configuration and in a head-to-tail configuration (FIG. 1B), which increases the potential target sites available for design of targeted nucleases at least 3-fold as compared currently-used architecture. Furthermore, the linkers described herein allow cleavage when the target sites of a pair of zinc finger nucleases are not 0-6 base pairs apart, for example target sites that are 7, 8, 9, 10 or more base pairs apart. The linker sequences described herein are typically between about 8 and 17 amino acids in length and may link to either N-terminal or C-terminal of a protein DNA-binding domain to a cleavage domain or, alternatively, may associate with any portion of a polynucleotide DNA-binding domain. In certain embodiments, the linker extends between the N- or C-terminal residue of a protein DNA-binding domain and the N- or C-terminal residue of the cleavage domain. In certain embodiments, the linkers extend between the N-terminal of the cleavage domain the DNA-binding domain.

Non-limiting examples of linkers as described herein are shown in FIGS. 3, 4, 5, 6, 7, 10, 11 and 19B.

The fusion molecules described herein may also include alterations to the N-terminal region of the selected cleavage domain. Alteration may include substitutions, additions and/or deletions of one or more N-terminal residues of the cleavage domain. In certain embodiments, the cleavage domain is derived from FokI and one or more amino acids of the wild-type FokI N-terminal region are replaced and additional amino acids added to this region. See, e.g., U.S. Patent Publication No. 2015/0064789.

Also described herein is a fusion protein comprising a DNA-binding domain, a modified FokI cleavage domain and a ZC linker between the DNA-binding domain and the FokI cleavage domain. The FokI cleavage domain may be modified in any way. Non-limiting examples of modifications include additions, deletions and/or substitutions to the N-terminal region of FokI (residues 158-169 of SEQ ID NO:282. See, e.g., U.S. Patent Publication No. 2009/0305419. In certain embodiments, the modified FokI cleavage domain comprises deletion of 1, 2, 3, 4 or more amino acids from the N-terminal region of FokI (e.g., deletion of one or more of residues 158, 159, 160 and/or 161 of the wild-type FokI domain as shown in SEQ ID NO:282)). In other embodiments, the modified FokI cleavage domain comprises one or more deletions and one or more substitutions from the N-terminal region of FokI (e.g., deletion of one or more of residues 158-161 and substitution of one or more of the remaining residues). Non-limiting examples of proteins with deletions and substitutions in the N-terminal FokI amino acid residues include the proteins designated V2, V4, V5, V6 and V8 as shown in FIG. 15. In other embodiments, the modified FokI cleavage domain comprises one or more substitutions in the N-terminal region of FokI. Non-limiting examples of proteins with substitutions in the N-terminal amino acid residues of FokI include the proteins designated V9 through V16 as shown in FIG. 15. In still further embodiments, the modified FokI cleavage domain comprises one or more additional amino acid residues (e.g., 1, 2, 3, 4 or more) N-terminal to the N-terminal-most residue of FokI (residue 158 of SEQ ID NO:282). In other embodiments, the modified FokI cleavage domain comprises one or more additional amino acid residues (e.g., 1, 2, 3, 4 or more) N-terminal to the N-terminal-most residue of FokI (residue 158 of SEQ ID NO:282) and one or more substitutions within the N-terminal region of FokI. Non-limiting examples of proteins with additions include those shown in FIG. 15 or FIG. 16 and substitutions within the N-terminal FokI amino acid residues as described in U.S. Patent Publication No 2009/0305419.

Typically, the linkers of the invention are made by making recombinant nucleic acids encoding the linker and the DNA-binding domains, which are fused via the linker amino acid sequence. Optionally, the linkers can also be made using peptide synthesis, and then linked to the polypeptide DNA-binding domains.

Nucleases

The linker sequences described herein are advantageously used to link DNA-binding domains, for example zinc finger proteins, TALEs, homing endonucleases, CRISPR/Cas guide RNAs and/or Ttago guide RNAs, to nuclease cleavage domains or half domains to form specifically targeted, non-naturally occurring nucleases. The DNA-binding domain may bind to any target sequence within the gene, including, but not limited to, any target sequence of 12 or more nucleotides in any genomic sequence.

A. DNA-Binding Domains

Any DNA-binding domain can be used in the methods disclosed herein.

In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in co-owned International Patent Publication No. WO 02/077227.

Selection of target sites; ZFPs and methods for design and construction of fusion proteins (and polynucleotides encoding same) are known to those of skill in the art and described in detail in U.S. Patent Publication Nos. 2005/0064474 and 2006/0188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family ("LAGLIDADG" is disclosed as SEQ ID NO:284), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22; 1125-1127; Jasin (1996) *Trends Genet.* 12:224-228; Gimble et al. (1996)*J Mol. Biol.*

263:163-180; Argast et al. (1998) *J Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 2007/0117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like (TAL) effectors which mimic plant transcriptional activators and manipulate the plant transcriptome (see Kay et al. (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al. (1989) Mol Gen Genet 218:127-136 and International Patent Publication No. WO 2010/079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack et al. (2006) *J Plant Physiol* 163(3):256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al. (2007) *Appl and Envir Micro* 73(13):4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues (RVD) at positions 12 and 13 with the identity of the contiguous nucleotides in the TAL-effector's target sequence (see Moscou and Bogdanove (2009) *Science* 326: 1501 and Boch et al. (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN). See, e.g., U.S. Pat. No. 8,586,526; Christian et al. ((2010)<Genetics epub 10.1534/genetics.110.120717). In certain embodiments, TALE domain comprises an N-cap and/or C-cap as described in U.S. Pat. No. 8,586,526. In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al. (2013) *Nat Comm:*1-8 DOI:10.1038/ncomms2782). Any TALENs may be used in combination with additional TALENs (e.g., one or more TALENs (cTALENs or FokI-TALENs) with one or more mega-TALs).

In certain embodiments, the DNA-binding domain is part of a CRISPR/Cas nuclease system. See, e.g., U.S. Pat. No. 8,697,359 and U.S. Patent Publication No. 2015/0056705. The CRISPR (clustered regularly interspaced short palindromic repeats) locus, which encodes RNA components of the system, and the Cas (CRISPR-associated) locus, which encodes proteins (Jansen et al. (2002) *Mol. Microbiol.* 43:1565-1575; Makarova et al. (2002) *Nucleic Acids Res.* 30:482-496; Makarova et al. (2006) *Biol. Direct* 1:7; Haft et al. (2005) *PLoSComput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, the DNA binding domain is part of a TtAgo system (see Swarts et al., ibid; Sheng et al., ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344:972-973). In contrast, prokaryotic Ago proteins bind to small single-stranded DNA fragments and likely function to detect and remove foreign (often viral) DNA (Yuan et al. (2005) *Mol. Cell* 19:405; Olovnikov et al. (2013) *Mol. Cell* 51:594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al., ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olovnikov et al., ibid).

Exogenous guide DNAs of arbitrary DNA sequence can be loaded onto the TtAgo protein (Swarts et al., ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to effect a panopoly of outcomes including gene knock-out, targeted gene addition, gene correction, targeted gene deletion using techniques standard in the art for exploitation of DNA breaks.

B. Cleavage Domains

The nucleases described herein (e.g., ZFNs, TALENs, CRISPR/Cas nuclease) also comprise a nuclease (cleavage domain, cleavage half-domain). The nuclease(s) can induce a double-stranded (DSB) or single-stranded break (nick) in the target DNA. In some embodiments, two nickases are used to create a DSB by introducing two nicks. In some cases, the nickase is a ZFN, while in others, the nickase is a TALEN or a CRISPR/Cas nickase.

The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, MA; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof).

In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease, or a DNA binding domain from a CRISPR/Cas system and a cleavage domain from a difference nuclease. Heterologous cleavage domains can be obtained from any endonuclease or exonuclease. Exemplary endonucleases from which a cleavage domain can be derived include, but are not limited to, restriction endonucleases and homing endonucleases. Additional enzymes which cleave DNA are known (e.g., S1 Nuclease;

mung bean nuclease; pancreatic DNase I; micrococcal nuclease; yeast HO endonuclease. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150; and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered. The wild-type sequence of FokI (SEQ ID NO:282) is shown below:

MDYKDHDGDYKDHDIDYKDDDDKMAPKKKRKVGIHGVPAAMAERPFQCRI

CMRNFSDRSNLSRHIRTHTGEKPFACDICGRKFAISSNLNSHTKIHTGSQ

KPFQCRICMRNFSRSDNLARHIRTHTGEKPFACDICGRKFATSGNLTRHT

KIHLRGSQLVKSELEEKKSELRHKLKYVPHEYIELIEIARNSTQDRILEM

KVMEFFMKVYGYRGKHLGGSRKPDGAIYTVGSPIDYGVIVDTKAYSGGYN

LPIGQADEMQRYVEENQTRNKHINPNEWWKVYPSSVTEFKFLEVSGHFKG

NYKAQLTRLNHITNCNGAVLSVEELLIGGEMIKAGTLTLEEVRRKENNGE

INF

An exemplary Type IIS restriction enzyme, whose cleavage domain is separable from the binding domain, is FokI. This particular enzyme is active as a dimer. Bitinaite et al. (1998) *Proc. Natl. Acad. Sci. USA* 95:10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,623,618; 8,409,861; 8,034,598; 7,914,796; and 7,888,121, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Pat. No. 7,888,121, the disclosure of which is incorporated by reference in its entirety for all purposes.

Cleavage domains with more than one mutation may be used, for example mutations at positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L;" mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE"

domains, respectively); engineered cleavage half-domain comprising mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively); and/or engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598 and 8,623,618, the disclosures of which are incorporated by reference in its entirety for all purposes. In other embodiments, the engineered cleavage half domain comprises the "Sharkey" and/or "Sharkey mutations" (see Guo et al. (2010) *J. Mol. Biol.* 400(1):96-107).

Alternatively, nucleases may be assembled in vivo at the nucleic acid target site using so-called "split-enzyme" technology (see e.g., U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al. (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek et al. (2012) *Science* 337 (6096):816-21; Jinek et al. (2013) *eLife* 2:e00471 and Cong, ibid).

Target Sites

As described in detail above, DNA-binding domains of the fusion molecules comprising the linkers as described herein can be engineered to bind to any sequence of choice. An engineered DNA-binding domain can have a novel binding specificity, compared to a naturally-occurring DNA-binding domain.

Non-limiting examples of suitable target genes a beta (β) globin gene (HBB), a gamma (γ) globin (also referred to as fetal globin) gene (HBG1), a B-cell lymphoma/leukemia 11A (BCL11A) gene, a Kruppel-like factor 1 (KLF1) gene, a CCR5 gene, a CXCR4 gene, a PPP1R12C (AAVS1) gene, an hypoxanthine phosphoribosyltransferase (HPRT) gene, an albumin gene, a Factor VIII gene, a Factor IX gene, a Leucine-rich repeat kinase 2 (LRRK2) gene, a Hungtingin (Htt) gene, a rhodopsin (RHO) gene, a Cystic Fibrosis Transmembrane Conductance Regulator (CFTR) gene, a surfactant protein B gene (SFTPB), a T-cell receptor alpha (TRAC) gene, a T-cell receptor beta (TRBC) gene, a programmed cell death 1 (PD1) gene, a Cytotoxic T-Lymphocyte Antigen 4 (CTLA-4) gene, an human leukocyte antigen (HLA) A gene, an HLA B gene, an HLA C gene, an HLA-DPA gene, an HLA-DQ gene, an HLA-DRA gene, a LMP7 gene, a Transporter associated with Antigen Processing (TAP) 1 gene, a TAP2 gene, a tapasin gene (TAPBP), a class II major histocompatibility complex transactivator (CIITA) gene, a dystrophin gene (DMD), a glucocorticoid receptor gene (GR), an IL2RG gene, a Rag-1 gene, an RFXS gene, a FAD2 gene, a FAD3 gene, a ZP15 gene, a KASII gene, a MDH gene, and/or an EPSPS gene.

In certain embodiments, the nuclease targets a "safe harbor" loci such as the AAVS1, HPRT, albumin and CCR5 genes in human cells, and Rosa26 in murine cells (see, e.g., U.S. Pat. Nos. 8,771,985; 8,110,379; and 7,951,925; U.S. Patent Publication Nos. 2010/0218264; 2011/0265198; 2013/0137104; 2013/0122591; 2013/0177983; 2013/0177960; 2015/0056705; and 2015/0159172), and the Zp15 locus in plants (see U.S. Pat. No. 8,329,986).

Donors

In certain embodiments, the present disclosure relates to nuclease-mediated modification of the genome of a cell, for instance a stem cell. As noted above, insertion of an exogenous sequence (also called a "donor sequence" or "donor" or "transgene"), for example for deletion of a specified region and/or correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest or can be integrated via non-homology directed repair mechanisms. Additionally, donor sequences can comprise a vector molecule containing sequences that are not homologous to the region of interest in cellular chromatin. A donor molecule can contain several, discontinuous regions of homology to cellular chromatin. Further, for targeted insertion of sequences not normally present in a region of interest, said sequences can be present in a donor nucleic acid molecule and flanked by regions of homology to sequence in the region of interest.

As with nucleases, the donors can be introduced in any form. In certain embodiments, the donors are introduced in mRNA form to eliminate residual virus in the modified cells. In other embodiments, the donors may be introduced using DNA and/or viral vectors by methods known in the art. See, e.g., U.S. Patent Publication Nos. 2010/0047805 and 2011/0207221. The donor may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In certain embodiments, the donor includes sequences (e.g., coding sequences, also referred to as transgenes) greater than 1 kb in length, for example between 2 and 200 kb, between 2 and 10 kb (or any value therebetween). The donor may also include at least one nuclease target site. In certain embodiments, the donor includes at least 2 target sites, for example for a pair of ZFNs, TALENs, TtAgo or CRISPR/Cas nucleases. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor can be inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter. The donor molecule may be inserted into an endogenous gene such that all, some or none of the endogenous gene is expressed. Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In some embodiments, the donor further comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

In certain embodiments, the transgene may include, for example, wild-type genes to replace mutated endogenous sequences. For example, a wild-type (or other functional) gene sequence may be inserted into the genome of a stem cell in which the endogenous copy of the gene is mutated. The transgene may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes). Exemplary splice acceptor site sequences are known to those of skill in the art and include, by way of example only, CTGACCTCTTCTCTTCCTCCCACAG, (SEQ ID NO:285) (from the human HBB gene) and TTTCTCTC-CACAG (SEQ ID NO:286) (from the human Immunoglobulin-gamma gene).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases, polynucleotides encoding these nucleases, donor polynucleotides and compositions comprising the proteins and/or polynucleotides described herein may be delivered by any suitable means. In certain embodiments, the nucleases and/or donors are delivered in vivo. In other embodiments, the nucleases and/or donors are delivered to isolated cells (e.g., autologous or heterologous stem cells) for the provision of modified cells (e.g., stem cells) useful in ex vivo delivery to patients.

Methods of delivering nucleases as described herein are described, for example, in U.S. Pat. Nos. 7,888,121; 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using any nucleic acid delivery mechanism, including naked DNA and/or RNA (e.g., mRNA) and vectors containing sequences encoding one or more of the components. Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. See, also, U.S. Pat. Nos. 6,534,261; 6,607,882; 6,824,978; 6,933,113; 6,979,539; 7,013,219; 7,163,824; and 10,604,771, incorporated by reference herein in their entireties. Furthermore, it will be apparent that any of these systems may comprise one or more of the sequences needed for treatment. Thus, when one or more nucleases and a donor construct are introduced into the cell, the nucleases and/or donor polynucleotide may be carried on the same delivery system or on different delivery mechanisms. When multiple systems are used, each delivery mechanism may comprise a sequence encoding one or multiple nucleases and/or donor constructs (e.g., mRNA encoding one or more nucleases and/or mRNA or AAV carrying one or more donor constructs).

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell.

Methods of non-viral delivery of nucleic acids include electroporation, lipofection, microinjection, biolistics, virosomes, liposomes, immunoliposomes, nanoparticles, polycation or lipid:nucleic acid conjugates, naked DNA, naked RNA, capped RNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Maryland), BTX Molecular Delivery Systems (Holliston, MA) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, International Patent Publication Nos. WO 91/17424 and WO 91/16024.

The use of RNA or DNA viral based systems for the delivery of nucleic acids encoding engineered CRISPR/Cas systems take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof.

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al. (1987) *Virology* 160:38-47; U.S. Pat. No. 4,797,368; International Patent Publication No. WO 93/24641; Kotin (1994) *Human Gene Therapy* 5:793-801; Muzyczka (1994) *J. Clin. Invest.* 94:1351. Construction of recombinant AAV vectors are described in a number of publications, including U.S. Pat. No. 5,173,414; Tratschin et al. (1985) *Mol. Cell. Biol.* 5:3251-3260; Tratschin et al. (1984) *Mol. Cell. Biol.* 4:2072-2081; Hermonat & Muzyczka (1984) *PNAS* 81:6466-6470; and Samulski et al. (1989) *J. Virol.* 63:03822-3828. Any AAV serotype can be used, including AAV1, AAV3, AAV4, AAV5, AAV6 and AAV8, AAV 8.2, AAV9, and AAV rh10 and pseudotyped AAV such as AAV2/8, AAV2/5 and AAV2/6.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) *Blood* 85:3048-305; Kohn et al. (1995) *Nat. Med.* 1:1017-102; Malech et al. (1997) *PNAS* 94(22):12133-12138). PA317/pLASN was the first therapeutic vector used in a gene therapy trial. (Blaese et al. (1995) *Science* 270:475-480). Transduction efficiencies of 50% or greater have been observed for MFG-S packaged vectors. (Ellem et al. (1997) *Immunol Immunother.* 44(1):10-20; Dranoff et al. (1997) *Hum. Gene Ther.* 1:111-2.

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner et al. (1998) *Lancet* 351(9117): 1702-3, Kearns et al. (1996) *Gene Ther.* 9:748-55). Other AAV serotypes, including AAV1, AAV3, AAV4, AAV5, AAV6, AAV8, AAV9 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al. (1998) *Hum. Gene Ther.* 7:1083-9). Additional examples of the use of adenovirus vectors for gene transfer in clinical trials include Rosenecker et al. (1996) *Infection* 24:1 5-10; Sterman et al. (1998) *Hum. Gene Ther.* 9(7):1083-1089; Welsh et al. (1995) *Hum. Gene Ther.* 2:205-18; Alvarez et al. (1997) *Hum. Gene Ther.* 5:597-613; Topf et al. (1998) *Gene Ther.* 5:507-513; Sterman et al. (1998) *Hum. Gene Ther.* 7:1083-1089.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. In addition, AAV can be manufactured using a baculovirus system (see e.g., U.S. Pat. Nos. 6,723,551 and 7,271,002).

Purification of AAV particles from a 293 or baculovirus system typically involves growth of the cells which produce the virus, followed by collection of the viral particles from the cell supernatant or lysing the cells and collecting the virus from the crude lysate. AAV is then purified by methods known in the art including ion exchange chromatography (e.g., see U.S. Pat. Nos. 7,419,817 and 6,989,264), ion exchange chromatography and CsCl density centrifugation (e.g., International Patent Publication No. WO 2011/094198 A10), immunoaffinity chromatography (e.g., International Patent Publication No. WO 2016/128408) or purification using AVB Sepharose (e.g., GE Healthcare Life Sciences).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

It will be apparent that the nuclease-encoding sequences and donor constructs can be delivered using the same or different systems. For example, a donor polynucleotide can be carried by an AAV, while the one or more nucleases can be carried by mRNA. Furthermore, the different systems can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Kits

Also provided are kits comprising any of the linkers described herein and/or for performing any of the above methods. The kits typically contain a linker sequence as described herein (or a polynucleotide encoding a linker as described herein). The kit may supply the linker alone or may provide vectors into which a DNA-binding domain and/or nuclease of choice can be readily inserted into. The kits can also contain cells, buffers for transformation of cells, culture media for cells, and/or buffers for performing assays. Typically, the kits also contain a label which includes any material such as instructions, packaging or advertising leaflet that is attached to or otherwise accompanies the other components of the kit.

Applications

The disclosed linkers are advantageously used to link with engineered DNA-binding domains with cleavage domains to form nucleases for cleaving DNA. The linkers as described herein allow for the cleavage of DNA when the target sites of a pair of nucleases used for cleavage are of variable spacings, for example target sites that are not 5 or 6 base pairs apart (e.g., 7, 8, 9 or more base pairs apart). Cleavage can be at a region of interest in cellular chromatin (e.g., at a desired or predetermined site in a genome, for example, in a gene, either mutant or wild-type); to replace a genomic sequence (e.g., a region of interest in cellular chromatin) with a homologous non-identical sequence (i.e., targeted recombination); to delete a genomic sequence by cleaving DNA at one or more sites in the genome, which cleavage sites are then joined by non-homologous end joining (NHEJ); to screen for cellular factors that facilitate homologous recombination; and/or to replace a wild-type sequence with a mutant sequence, or to convert one allele to a different allele. Such methods are described in detail, for example, in U.S. Pat. No. 7,888,121, incorporated by reference in its entirety herein.

Accordingly, the disclosed linkers can be used in any method in which specifically targeted cleavage is desirable and/or to replace any genomic sequence with a homologous, non-identical sequence. For example, a mutant genomic sequence can be replaced by its wild-type counterpart, thereby providing methods for treatment of e.g., genetic disease, inherited disorders, cancer, and autoimmune disease. In like fashion, one allele of a gene can be replaced by a different allele using the methods of targeted recombination disclosed herein. Indeed, any pathology dependent upon a particular genomic sequence, in any fashion, can be corrected or alleviated using the methods and compositions disclosed herein.

Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, Alsheimer's disease, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, Parkinson's disease, *porphyria*, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240) and X-linked SCID.

Additional exemplary diseases that can be treated by targeted DNA cleavage and/or homologous recombination include acquired immunodeficiencies, lysosomal storage diseases (e.g., Gaucher's disease, GM1, Fabry disease and Tay-Sachs disease), mucopolysaccahidosis (e.g., Hunter's disease, Hurler's disease), hemoglobinopathies (e.g., sickle cell diseases, HbC, α-thalassemia, β-thalassemia) and hemophilias.

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. See, International Patent Publication No. WO 2007/139982. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g., Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR-5 and CXCR-4.

Nucleases containing the disclosed linkers can also be used for inactivation (partial or complete) of one or more genomic sequences. Inactivation can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause mis-splicing of the transcript.

Nuclease-mediated inactivation (e.g., knockout) of endogenous genes can be used, for example, to generate cell lines deficient in genes involved in apoptosis or protein production (e.g., post-translational modifications such as fucosylation). ZFN-mediated inactivation can also be used to generate transgenic organisms (e.g., plants, rodents and rabbits).

In addition, because nucleases don't appear to have specificity for the DNA sequence between the two paired half sites, nucleases with linkers as described herein can be designed to cleave DNA such that the resulting single-stranded overhangs have any desired sequence. In particular, linkers as described herein can be designed to influence both the size and position of these single-stranded overhangs with respect to the starting sequence. Thus, when incorporated into one or more nucleases of a nuclease pair, linkers as described herein can result in more uniform ends following cleavage. Accordingly, the linkers described herein can also be used to more efficiently clone DNA cut with nucleases, which is broadly applicable in many areas of biotechnology and basic science.

Thus, the linkers described herein provide broad utility for improving nuclease-mediated cleavage in gene modification applications. Linkers as described herein may be readily incorporated into any existing nuclease by either site directed mutagenesis or subcloning to be used in many applications in standard cloning, constructing large genomes for synthetic biology, new types of RFLP analysis of large sequences or even allow new types of cloning involving extremely large DNA sequences. The potential properties of nucleases with rigid linkers could also be ideal in applications such as DNA computing.

The following Examples relate to exemplary embodiments of the present disclosure in which the nuclease comprises one or more ZFNs. It will be appreciated that this is for purposes of exemplification only and that other DNA-binding domains can be used, for instance TAL-effector DNA binding domains, sgRNAs (CRISPR/Cas nuclease systems), etc. Other nucleases may also be used including homing endonucleases (meganucleases) with engineered DNA-binding domains and/or fusions of naturally occurring of engineered homing endonucleases (meganucleases) DNA-binding domains and heterologous cleavage domains, and nuclease systems such as TtAgo and CRISPR/Cas using engineered single guide RNAs.

EXAMPLES

Example 1: Selection of Linkers

Figure 2:
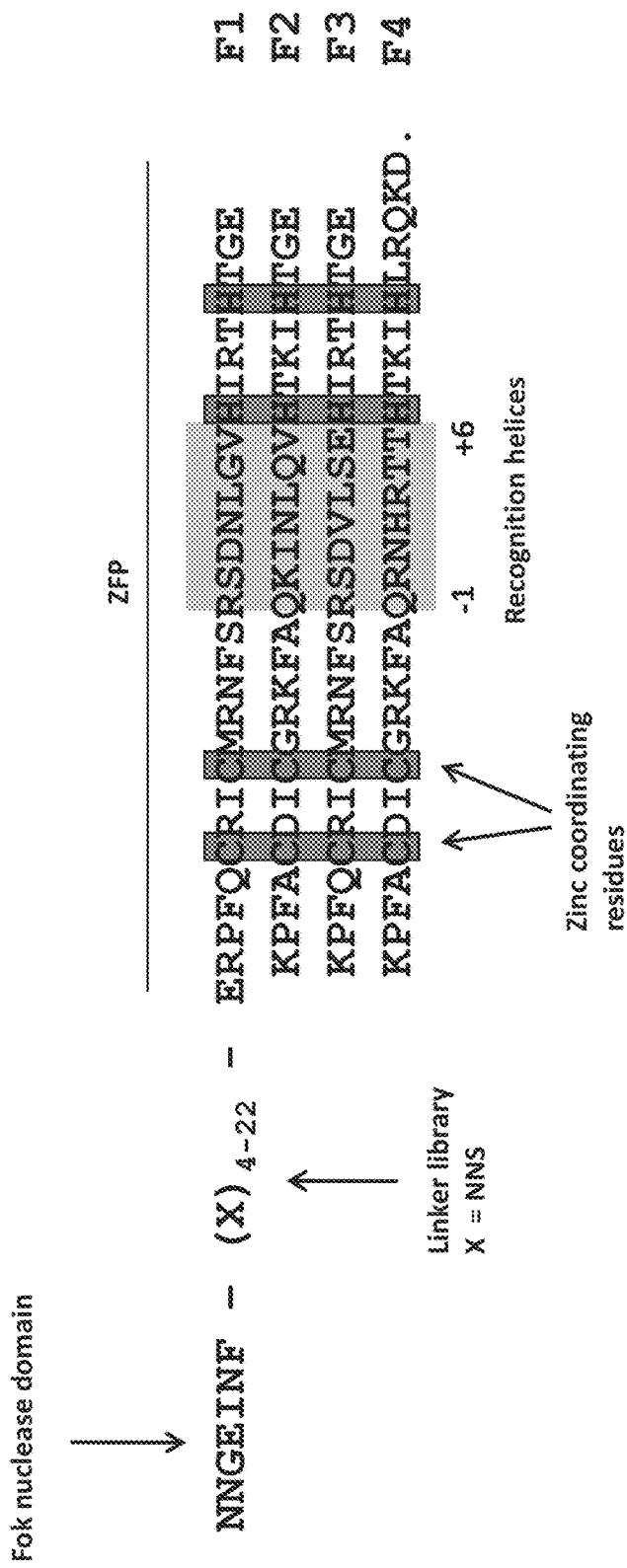
FIG. 2 depicts the design of the FokI-ZFP linker library used for the selections. A linker randomized in both length and composition was cloned between an N-terminal FokI domain (SEQ ID NO:1) and a C-terminal ZFP domain (exemplary sequences shown in SEQ ID NOs:2-5).

Linkers were selected from a bacterial selection system as described in U.S. Patent Publication No. 2015/0064789. Fully randomized linker libraries of 4-22 amino acids were cloned between an N-terminal FokI domain and a C-terminal ZFP binding domain of one of the ZFNs in a ZFN dimer (FIG. 2). Selections were performed on targets with a 6, 7, 8, 9, 10, or 11 base pair spacing between the two DNA-binding domain (ZFN) binding sites, where the binding sites were on the same strand of DNA.

For the selection, bacteria were transformed with a ZFN-encoding plasmid (expression of the ZFN driven by the arabinose inducible promoter) and a plasmid (pTox) that expressed the bacterial ccdB toxin from the T7 promoter and included the ZFN target sites. This system allows the ability to query very large linker libraries with complexities of ~$10^8$ and a high stringency option (>100 cleavage events required for survival).

The expressed ZFN cleaved pTox leading to degradation of pTox; the ccdB toxin was then switched on for cell killing; the survivors (with ZFN-cleaved pTox) were amplified and the genes encoding the linkers re-cloned into new plasmids for the next cycle. Linkers were sequenced after 4, 6, and 9 rounds of selection. Analysis of the selected linkers showed length trends that were correlated with the length of the spacer between the binding sites. Selected linker sequences are shown in FIGS. 4-8 and 11.

Example 2: In Vivo Activity

Linkers were then screened for activity in vivo. Zinc finger nuclease constructs targeted to CCR5 and AAVS1 target sites (but on the same DNA strand) were prepared using selected linkers fusing cleavage domains (wild-type or engineered FokI) to zinc finger DNA-binding domains disclosed in U.S. Pat. No. 7,951,925 (CCR5) and U.S. Pat. No. 8,110,379 (AAVS1).

Since the selected architecture is not found in the human genome, K562 cells were engineered to have a head-to-tail CCR5 target site with the indicated gap spacings at the AAVS1 locus. A second set of cell lines were engineered with the AAVS1 target site in a head-to-tail configuration at the CCR5 locus using the best-performing linkers from the head-to-tail CCR5 screen. The selected linkers were tested as ZFNs on the gap spacings for which they were selected.

Figure 9:
FIG. 9 is a summary of results obtained with the linkers (from the top, SEQ ID NOs:78, 80, 62, 71, 81, 82, 83, 9, 36, 16, 72, 69, 84, 55, 37, 51, 77, 45, 40, 10, 41, 47, 24, 63, and 39 (6 bp spacing) and from the top, SEQ ID NOs:114, 138, 100, 91, 109, 154, 147, 136, 88, 160, 142, 161, 132 and 93 (7 bp spacing)) tested in vivo within nucleases targeted to CCR5 or AAVS1. Cell lines were generated where the AAVS1 locus was modified to have a head-to-tail CCR5 target site with either a 6 or 7 base pair spacing. NHEJ activity for linkers tested at these sites is located in the "CCR5" column. Likewise, cell lines were generated where the CCR5 locus was modified to have a head-to-tail AAVS1 target site with either a 6 or 7 base pair spacing. NHEJ activity for linkers tested at these sites is located in the "AAVS1" column. The shaded boxes indicate linkers used in further studies.

As shown in FIGS. 9 and 10, many linkers were identified that showed activity similar to or better than the tail-to-tail controls at the exemplary CCR5 and AAVS1 loci.

The data demonstrate that nucleases comprising the linkers described are active when the target sites are on the same strand (head-to-tail configuration).

Example 3: Portability Studies

From the previous two screens the top 8 linkers for each of the 6 and 7 base pair spacings (shown in FIG. 11) were chosen for further testing. The experimental design of this portability study is shown in FIG. 12. Ten ZFN pairs were designed to the CTLA4 gene for each of the three following architectures: 1) tail-to-tail, 2) head-to-tail with a 6 base pair spacing, and 3) tail-to-tail with a 7 base pair spacing. For the head-to-tail architectures the set of 10 ZFN pairs were tested with each of the top 8 linkers for each spacing. For the 7 base pair spacing the constant ZFN contained either a standard (L0) or an extended linker (L7c5). An additional 2 linkers selected for an 8 base pair spacing were also included. Transfections were done in K562 cells.

FIGS. 13 and 14 show the NHEJ activity for each of the pairs in the portability study that used the standard linker (L0) in the constant ZFN. The 10 ZFN pairs are listed down the left side and the 8 linkers are listed across the top. Below are the 10 tail-to-tail ZFN pairs. As shown in the Figures, the average activity for the best linkers for a 6 and 7 base pair spaced head-to-tail ZFNs was higher than the average for the tail-to-tail architecture.

FIG. 15 shows a comparison of the NHEJ activity of 6 of the ZFNs from FIGS. 13 and 14 in the head-to-tail configuration. Here the polarity of the FokI domain was switched between the two ZFNs in each pair. These results show that the selected linkers enable highly-active ZFNs in either obligate heterodimer FokI polarity.

Figure 17:
FIG. 17 is a summary of NHEJ activity of AAVS1-targeted nucleases with the indicated linkers in the tail-to-tail configuration (left panel); head-to-tail 6 bp spacing configuration (middle panel) and head-to-tail 7 bp spacing configuration (right panel). The ZFNs were targeted to intron 1 of the AAVS1 gene excluding the hypersentive site (FIG. 16).

FIGS. 16 and 17 show the NHEJ activity for ZFNs designed to AAVS1 intron 1 that compare the top 3 linkers for each of the 6 (N6a, N6b, N6c) and 7 (N7a, N7b, N7c) base pair spacings. FIG. 16 shows ZFNs targeted to a hypersensitive site within intron of the AAVS1 gene whereas FIG. 17 shows ZFNs targeted to the all of intron 1 of the AAVS1 gene excluding the hypersensitive site. Nineteen ZFN pairs were designed for each of the following architectures: 1) tail-to-tail architecture, 2) head-to-tail architecture with a 6 base pair spacing, and 3) head-to-tail architecture with a 7 base pair spacing. The data show that the linkers described enable ZFNs with a head-to-tail architecture that are highly active across multiple genes and designs.

Example 4: Head-to-Head Architecture

The two best linkers for each of the 6 and 7 base pair spacings identified in Example 3 were then chosen to test in the head-to-head architecture (see, FIG. 1C). Eleven pairs were designed for each of 5, 6, 7, 8, or 9 base pair spacings. The 6, 7, and 8 base pair spacings used all four of the linkers whereas the 5 base pair spacing used only the two best 6 base pair linkers and the 9 base pair spacing used only the two best 7 base pair linkers.

As shown in FIG. 18, high levels of gene modification at 7, 8 and 9 base pair spacings with all the linkers tested were achieved.

Thus, the linkers described herein show high activity when incorporated in nucleases designed to bind to target sites on the same DNA strand (e.g., head-to-tail architecture) or target sites on opposite DNA stands (e.g., head-to-head architecture) in a reversed architecture from the standard (e.g., tail-to-tail architecture).

Example 5: Tail-to-Tail Architecture with Expanded Spacing

Selections were also performed for ZFNs in a tail-to-tail architecture with either a 7, 8, or 9 base pair spacing as compared to conventional ZFNs which use a 5 to 6 base pair spacing. The setup for the ZFNs in the selection is shown in FIG. 19A. For the case where both ZFNs contain the same selected linker (FIG. 19A top), this architecture is called symmetric tail-to-tail. This architecture was selected using a single ZFN with the linker library and a homodimeric target site. For the case where one ZFN contains the selected linker and the other ZFN contains the L0 linker (i.e. LRGSQLVKS, SEQ ID NO:283), this architecture is called asymmetric tail-to-tail. This architecture was selected using a constant ZFN with the L0 linker and one containing the linker library on a heterodimeric target site. Selections were performed as in Example 1 and U.S. Patent Publication No. 2015/0064789.

FIG. 19B shows the exemplary linkers for each architecture configuration and spacing that were tested in vivo. K562 cells were engineered to have the CCR5 target site with the indicated spacing at the CCR5 locus. Shown are the top performing linkers for each of these configurations using the CCR5 ZFNs. Also shown in the table are positive control AAVS1 ZFNs for each of the cell lines. The data show that ZFNs using either the asymmetric or symmetric tail-to-tail configuration at larger than standard spacings worked as well as typical tail-to-tail ZFNs.

Exemplary linkers from FIG. 19B are used for further testing in a portability study. Eight ZFN pairs are designed for each of the following architectures: 1) tail-to-tail with a 5 or 6 basepair spacing (for comparison), 2) tail-to-tail with a 7 basepair spacing, 3) tail-to-tail with a 8 basepair spacing, and 4) tail-to-tail with a 9 basepair spacing. For the 7, 8, and 9 basepair spacings the panel of exemplary linkers are cloned into one ZFN of the pair and tested in vivo (in a similar fashion to Example 3). All ZFNs are shown to be active.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A dimer comprising first and second fusion molecules, the first fusion molecule comprising a DNA binding domain that binds to a first target site and a first wild-type or engineered cleavage domain and the second fusion molecule comprising a DNA-binding domain that binds to a second target site and a second wild-type or engineered cleavage domain, wherein the first and second cleavage domains dimerize when the DNA-binding domains are bound to the first and second target sites separated by 7 base pairs, wherein the first fusion molecule comprises an amino acid linker between the DNA-binding domain and the first cleavage domain, wherein the linker is selected from the group consisting of:

SGERRQSHVL; (SEQ ID NO: 114)

SGAIRCHDEFWF; (SEQ ID NO: 100)

SGALQEPWSI; (SEQ ID NO: 91)

SGFNHSSCDVVY; (SEQ ID NO: 138)

QSGKIASPHVVI; (SEQ ID NO: 147)

SGTPHEVGVYTL; (SEQ ID NO: 154)

MGDEHRKLRLMSQMRLQVD; (SEQ ID NO: 254)

KPRTDRKIFSLRLAN; (SEQ ID NO: 255)

NPLPRNKYPSPYFLH; (SEQ ID NO: 266)

APPAASKSRTWEMRR; (SEQ ID NO: 267)

LNRPKLNTRPHYTSV; (SEQ ID NO: 268)
and

QTRPPRSFCMLAMTG. (SEQ ID NO: 269)

2. A dimer according to claim 1, wherein the DNA-binding domains comprises a zinc finger protein, a TAL-effector domain or a single guide RNA (sgRNA).

3. A dimer according to claim 1, wherein the linker extends between the N-terminal of the DNA-binding domain and C-terminal of the cleavage domain.

4. The dimer according to claim 1 wherein the linker comprises

SGTPHEVGVYTL (SEQ ID NO: 154)
or

SGAIRCHDEFWF. (SEQ ID NO: 100)

5. The dimer according to claim 1, wherein the DNA-binding domains bind to opposite or the same strand of DNA in a double-stranded target DNA.

6. The dimer according to claim 1, wherein the dimer makes a double- or single-stranded cut in a target double-stranded DNA.

7. A polynucleotide encoding the dimer of claim 1.

8. An isolated cell comprising one or more dimers according to claim 1.

9. A method of modifying cellular chromatin in a cell, the method comprising:
cleaving the cellular chromatin with a dimer according to claim 1 such that the cellular chromatin is modified, wherein the dimer is introduced into the cell using one or more polynucleotides.

10. The method according to claim 9, wherein the modification comprises introducing an insertion and/or deletion into the cellular chromatin.

11. The method according to claim 9, wherein the modification comprises integration of a donor sequence.

12. A kit comprising a dimer according to claim 1.

13. A dimer comprising first and second fusion molecules, the first fusion molecule comprising a DNA binding domain that binds to a first target site and a first wild-type or engineered cleavage domain and the second fusion molecule comprising a DNA-binding domain that binds to a second target site and a second wild-type or engineered cleavage domain, wherein the first and second cleavage domains dimerize when the DNA-binding domains are bound to the first and second target sites separated by 8 base pairs, wherein the first fusion molecule comprises an amino acid linker between the DNA-binding domain and the first cleavage domain, wherein the linker is selected from the group consisting of:

MHGPRLPPLKLCGAWSIG; (SEQ ID NO: 270)

GPRVVTRRVLATVTVA; (SEQ ID NO: 271)

LGMVSRPRLNQRAPIPKS; (SEQ ID NO: 272)

QYPRHPTTSKRIGPTDRVLT; (SEQ ID NO: 273)

YPREATSRRETDILNSKRLLS; (SEQ ID NO: 274)
and

QCNPVLKCRTIKPGPSAA. (SEQ ID NO: 275)

14. A dimer according to claim 13, wherein the DNA-binding domains comprises a zinc finger protein, a TAL-effector domain or a single guide RNA (sgRNA).

15. A dimer according to claim 13, wherein the linker extends between the N-terminal of the DNA-binding domain and C-terminal of the cleavage domain.

16. The dimer according to claim 13, wherein the DNA-binding domains bind to opposite or the same strand of DNA in a double-stranded target DNA.

17. The dimer according to claim 13, wherein the dimer makes a double- or single-stranded cut in a target double-stranded DNA.

18. A polynucleotide encoding the dimer of claim 13.

19. An isolated cell comprising one or more dimers according to claim 13.

20. A method of modifying cellular chromatin in a cell, the method comprising:
cleaving the cellular chromatin with a dimer according to claim 13 such that the cellular chromatin is modified, wherein the dimer is introduced into the cell using one or more polynucleotides.

21. The method according to claim 20, wherein the modification comprises introducing an insertion and/or deletion into the cellular chromatin.

22. The method according to claim 20, wherein the modification comprises integration of a donor sequence.

23. A kit comprising a dimer according to claim 13.

24. A dimer comprising first and second fusion molecules, the first fusion molecule comprising a DNA binding domain that binds to a first target site and a first wild-type or engineered cleavage domain and the second fusion molecule comprising a DNA-binding domain that binds to a second target site and a second wild-type or engineered cleavage domain, wherein the first and second cleavage domains dimerize when the DNA-binding domains are bound to the first and second target sites separated by 9 base pairs, wherein the first fusion molecule comprises an amino acid linker between the DNA-binding domain and the first cleavage domain, wherein the linker is selected from the group consisting of:

```
                                     (SEQ ID NO: 276)
QPTWMKSPRKKRYPTGRLTAQ;

(SEQ ID NO: 277)
DPEYLSQRVPRRRQKPPMTRPY;

(SEQ ID NO: 278)
MEQRVRATNPRRRLAILTTESFM;

(SEQ ID NO: 279)
QSPNMIQRTPKRRTPLTIPLR;

(SEQ ID NO: 280)
AGNCARLTVRPPFSHP;
and
                                     (SEQ ID NO: 281)
ERPPRSLASPPHALLL.
```

25. A dimer according to claim 24, wherein the DNA-binding domains comprises a zinc finger protein, a TAL-effector domain or a single guide RNA (sgRNA).

26. A dimer according to claim 24, wherein the linker extends between the N-terminal of the DNA-binding domain and C-terminal of the cleavage domain.

27. The dimer according to claim 24, wherein the DNA-binding domains bind to opposite or the same strand of DNA in a double-stranded target DNA.

28. The dimer according to claim 24, wherein the dimer makes a double- or single-stranded cut in a target double-stranded DNA.

29. A polynucleotide encoding the dimer of claim 24.

30. An isolated cell comprising one or more dimers according to claim 24.

31. A method of modifying cellular chromatin in a cell, the method comprising:
cleaving the cellular chromatin with a dimer according to claim 24 such that the cellular chromatin is modified, wherein the dimer is introduced into the cell using one or more polynucleotides.

32. The method according to claim 30, wherein the modification comprises introducing an insertion and/or deletion into the cellular chromatin.

33. The method according to claim 30, wherein the modification comprises integration of a donor sequence.

34. A kit comprising a dimer according to claim 24.

* * * * *